(12) United States Patent
Matula et al.

(10) Patent No.: US 11,698,364 B2
(45) Date of Patent: Jul. 11, 2023

(54) REAL-TIME CELL-SURFACE MARKER DETECTION

(71) Applicant: University of Washington, Seattle, WA (US)

(72) Inventors: Thomas J. Matula, Kirkland, WA (US); Masaoki Kawasumi, Seattle, WA (US); Oleg Sapozhnikov, Seattle, WA (US)

(73) Assignee: University of Washington, Seattle, WA (US)

( * ) Notice: Subject to any disclaimer, the term of this patent is extended or adjusted under 35 U.S.C. 154(b) by 803 days.

(21) Appl. No.: 16/455,550

(22) Filed: Jun. 27, 2019

(65) Prior Publication Data
US 2020/0001293 A1 Jan. 2, 2020

Related U.S. Application Data

(60) Provisional application No. 62/690,452, filed on Jun. 27, 2018.

(51) Int. Cl.
| | | |
|---|---|---|
| *G01N 33/49* | (2006.01) | |
| *B01L 3/00* | (2006.01) | |
| *G01N 33/58* | (2006.01) | |
| *G01N 15/10* | (2006.01) | |
| *G01N 33/50* | (2006.01) | |
| *G01N 15/14* | (2006.01) | |

(52) U.S. Cl.
CPC ...... *G01N 33/4915* (2013.01); *B01L 3/50273* (2013.01); *B01L 3/502761* (2013.01); *G01N 15/1056* (2013.01); *G01N 33/5014* (2013.01); *G01N 33/585* (2013.01); *B01L 2200/0647* (2013.01); *B01L 2400/0436* (2013.01); *G01N 2015/142* (2013.01); *G01N 2510/00* (2013.01)

(58) Field of Classification Search
CPC ............ G01N 33/4915; G01N 33/585; G01N 2015/142; B01L 3/50273; B01L 2400/0436
See application file for complete search history.

(56) References Cited

U.S. PATENT DOCUMENTS

| | | |
|---|---|---|
| 4,006,444 A | 2/1977 | Quate |
| 4,361,400 A | 11/1982 | Gray |
| 4,981,580 A | 1/1991 | Auer |

(Continued)

FOREIGN PATENT DOCUMENTS

| | | |
|---|---|---|
| CN | 104263644 A | 1/2015 |
| CN | 106729777 | 5/2017 |

(Continued)

OTHER PUBLICATIONS

Faridi et al. MicroBubble activated acoustic cell sorting. Biomed Microdevices 19 (23): 1-7 (Apr. 3, 2017).*

(Continued)

*Primary Examiner* — Gailene Gabel
(74) *Attorney, Agent, or Firm* — Christensen O'Connor, Johnson Kindness PLLC

(57) ABSTRACT

Cell-separation systems and methods utilizing cell-specific microbubble tags and ultrasound-based separation are described. The methods are useful for simplification of time-consuming and costly cell purification procedures and real time apoptosis detection.

10 Claims, 16 Drawing Sheets

(56) References Cited

U.S. PATENT DOCUMENTS

| | | |
|---|---|---|
| 5,348,002 A | 9/1994 | Caro |
| 5,483,469 A | 1/1996 | Van Den Engh |
| 5,641,457 A | 6/1997 | Vardanega |
| 5,853,994 A | 12/1998 | Gopinathan |
| 6,261,537 B1 | 7/2001 | Klaveness |
| 6,423,007 B2 | 7/2002 | Lizzi |
| 6,795,191 B2 | 9/2004 | Barbehenn |
| 7,081,192 B1 | 7/2006 | Wang |
| 7,374,744 B2 | 5/2008 | Schutt |
| 7,699,799 B2 | 4/2010 | Blanton |
| 7,804,595 B2 | 9/2010 | Matula |
| 8,264,683 B2 | 9/2012 | Matula |
| 8,441,624 B2 | 5/2013 | Matula |
| 10,161,926 B2 | 12/2018 | Gilmanshin |
| 2003/0003055 A1 | 1/2003 | Unger |
| 2004/0054357 A1 | 3/2004 | O'Donnell |
| 2004/0179200 A1 | 9/2004 | Yoon |
| 2006/0290944 A1 | 12/2006 | Arnott |
| 2007/0151905 A1 | 7/2007 | Wang |
| 2007/0197886 A1 | 8/2007 | Naganuma |
| 2008/0243049 A1 | 10/2008 | Hardy |
| 2008/0245745 A1 | 10/2008 | Ward |
| 2008/0247264 A1 | 10/2008 | Gabl |
| 2009/0029870 A1 | 1/2009 | Ward |
| 2009/0053686 A1* | 2/2009 | Ward ............... G01N 15/1404 435/173.9 |
| 2009/0316151 A1 | 12/2009 | Matula |
| 2010/0009333 A1 | 1/2010 | Auer |
| 2010/0135905 A1 | 6/2010 | Hallahan |
| 2011/0045095 A1 | 2/2011 | Hettiarachchi |
| 2011/0134426 A1 | 6/2011 | Kaduchak |
| 2011/0196637 A1 | 8/2011 | Sharpe |
| 2011/0208113 A1 | 8/2011 | Toma |
| 2011/0245750 A1 | 10/2011 | Lynch |
| 2012/0093730 A1 | 4/2012 | Malecki |
| 2012/0160746 A1 | 6/2012 | Thorslund |
| 2012/0225475 A1 | 9/2012 | Wagner |
| 2013/0043170 A1 | 2/2013 | Rose |
| 2013/0048565 A1 | 2/2013 | Fiering |
| 2014/0347669 A1 | 11/2014 | Matula |
| 2015/0017678 A1 | 1/2015 | Matula |
| 2016/0363579 A1 | 12/2016 | Gilmanshin |
| 2017/0074872 A1 | 3/2017 | Delouise |
| 2017/0260493 A1 | 9/2017 | Lipkens |
| 2017/0328334 A1 | 11/2017 | Sawdon |

FOREIGN PATENT DOCUMENTS

| | | |
|---|---|---|
| CN | 107625970 | 1/2018 |
| EP | 1673108 A2 | 6/2006 |
| WO | 2012135663 A2 | 10/2012 |
| WO | 2012135663 A3 | 12/2012 |
| WO | 2017190117 A1 | 11/2017 |
| WO | 2018009816 A1 | 1/2018 |
| WO | 2018112262 A2 | 6/2018 |

OTHER PUBLICATIONS

Liou et al. Buoyancy-Activated Cell Sorting Using Targeted Biotinylated Albumin Microbubbles PLoS ONE 10(5): e0125036. pp. 1-15 (May 20, 2015).*

Xiaoyu Shi. Buoyancy-based separation of antigen-specific T cells. University of California San Diego Electronic Theses and Dissertations. Retrieved from https://escholarship.org/uc/item/9g97509x. Abstract Only (2016).*

Maheswaran S, Haber DA. Ex Vivo Culture of CTCs: An Emerging Resource to Guide Cancer Therapy. Cancer Res. 2015;75(12):2411-5 PMID: 25998619. PMCID: PMC4470788.

Almeida M, Garcia-Montero AC, Orfao A. Cell purification: a new challenge for biobanks. Pathobiology. 2014,81(5-6):261-75. PMID: 25792215.

Boonstra MC, de Geus SW, Prevoo HA, Hawinkels LJ, van de Velde CJ, Kuppen PJ, Vahrmeijer AL, Sier CF. Selecting Targets for Tumor Imaging: An Overview of Cancer-Associated Membrane Proteins. Biomark Cancer. 2016;8:119-33. PMID: 27721658.

Lenshof A, Magnusson C, Laurell T. Acoustofluidics 8: applications of acoustophoresis in continuous flow microsystems. Lab Chip. 2012;12(7):1210-23. PMID: 22362021.

Goddard G, Martin JC, Graves SW, Kaduchak G. Ultrasonic particle-concentration for sheathless focusing of particles tor analysis in a flow cytometer. Cytometry A. 2006;69(2):66-74. PMID: 16419065.

Klibanov AL. Ligand-carrying gas-filled microbubbles: ultrasound contrast agents for targeted molecular imaging. Bioconjug Chem. 2005;16(1):9-17. PMID: 15656569.

Van Rooij T, Daeichin V, Skachkov I, de Jong N, Kooiman K. Targeted ultrasound contrast agents for ultrasound molecular imaging and therapy. Int J Hyperthermia. 2015;31(2):90-106. PMID: 25707815.

Unnikrishnan S, Klibanov AL. Microbubbles as ultrasound contrast agents for molecular imaging: preparation and application. AJR Am J Roentgenol. 2012;199(2):292-9. PMID: 22826389.

Al Saati T, Alibaud L, Lamant L, Boyes J, March M, Delsol G. A new monoclonal anti-CD7 antibody reactive on paraffin sections. Appl Immunohistochem Mol Morphol. 2001;9(4):289-96. PMID: 11759053.

Pontén F, Jirström K, Uhlen M. The Human Protein Attas—a tool for pathology. J Pathol. 2008;216(4):387-93. PMID: 18853439.

Hollingshead MG, Stockwin LH, Alcoser SY, Newton DL, Orsbum BC, Bonomi CA, Borgel SD, Divelbiss R, Dougherty KM, Hager EJ, Holbeck SL, Kaur G, Kimmel DJ, Kunkel MW, Millione A, Mullendore ME, Stotler H, Collins J. Gene expression profiling of 49 human tumor xenografts from in vitro culture through multiple in vivo passages—strategies for data mining in support of therapeutic studies. BMC Genomics. 2014;15:393. PMID: 24885658. PMCID: PMC4041995.

Mirkina I, Hadzijusufovic E, Krepler C, Mikula M, Mechtcheriakova D, Strommer S, Stella A, Jensen-Jarolim E, Höller C, Wacheck V, Pehamberger H, Valent P. Phenotyping of human melanoma cells reveals a unique composition of receptor targets and a subpopulation co-expressing ErbB4, EPO-R and NGF-R. PLoS One. 2014;9(1):e84417. PMID: 24489649. PMCID: PMC3906015.

Savage EC, Vanderheyden AD, Bell AM, Syrbu SI, Jensen CS. Independent diagnostic accuracy of flow cytometry obtained from fine-needle aspirates: a 10-year experience with 451 cases. Am J Clin Pathol. 2011;135(2):304-9. PMID: 21228371.

Adelmann CH, Ching G, Du L, Saporito RC, Bansal V, Pence LJ, Liang R, Lee W, Tsai KY. Comparative profiles of BRAF inhibitors: the paradox index as a predictor of clinical toxicity. Oncotarget. 2016;7(21):30453-60. PMID: 27028853. PMCID: PMC5058692.

Smalley KSM, Lioni M, Dalia Palma M, Xiao M, Desai B, Egyhazi S, Hansson J, Wu H, King AJ, Van Belle P, Elder DE, Flaherty KT, Herlyn M, Nathanson KL. Increased cyclin D1 expression can mediate BRAF inhibitor resistance in BRAF V600E-mutated melanomas. Mol Cancer Ther. 2008;7(9):2876-83. PMID: 18790768. PMCID: PMC2651569.

Schmitt MW, Kennedy SR, Salk JJ, Fox EJ, Hiatt JB, Loeb LA. Detection of ultra-rare mutations by next-generation sequencing. Proc Natl Acad Sci U S A. 2012;109(36):14508-13. PMID: 22853953. PMCID: PMC3437896.

Francis G. Blankenberg "In Vivo Detection of Apoptosis" The Journal of Nuclear Medicine, 2008 vol. 49: Issue 6 (Supplemental) p. 81S-95S.

Boriphat Methachan, Kamolrat Thanapprapasr "Polymer-Based Materials in Cancer Treatment: From Therapeutic Carrier and Ultrasound Contrast Agent to Theranostic Applications" Ultrasound in Medicine & Biology 2016 vol. Preprint p. 1-14.

Mochizuki, T et al. "Detection of Apoptotic Tumor Response In Vivo After a Single Dose of Chemotherapy with 99mTc-Annexin V" J Nucl Med Jan. 1, 2003 vol. 44 No. 1 92-97.

Schellenberger, E. A. et al. Optical imaging of apoptosis as a biomarker of tumor response to chemotherapy. Neoplasia May-Jun. 2003;5(3):187-92.

Wlodkowic, D., Skommer, J. & Darzynkiewicz, Z. Flow cytometry-based apoptosis detection. Methods Mol. Biol. (2009). 559:19-32.

(56) References Cited

OTHER PUBLICATIONS

Brown, M. & Wittwer, C. Flow Cytometry: Principles and Clinical Applications in Hematology. Clin. Chem. (2000). 46:8(B) 1221-1229.
Van Engeland, M., Nieland, L. J. W., Ramaekers, F. C. S., Schutte, B. & Reutelingsperger, C. P. M. Annexin V-Affinity assay: A review on an apoptosis detection system based on phosphatidylserine exposure. Cytometry (1998). 31:1-9.
Archana, M., Bastian, Yogesh, T. L. & Kumaraswamy, K. L. Various methods available for detection of apoptotic cells—a review. Indian J. Cancer (2013). Jul.-Sep; 50(3):274-83.
Perez, C. et al. Acoustic and optical characterization of ultrasound contrast agents via flow cytometry. J. Acoust. Soc. Am. (2012). 132, 1906.
Van Heerde, W. L. et al. Markers of apoptosis in cardiovascular tissues: focus on Annexin V. Cardiovasc. Res. vol. 45, Issue 3, Feb. 2000, pp. 549-559.
Krysko, O., de Ridder, L. & Cornelissen, M. Phosphatidylserine exposure during early primary necrosis (oncosis) in JB6 cells as evidenced by immunogold labeling technique. Apoptosis. Jul. 2004, vol. 9, Issue 3, pp. 495-500.
Wenpeng Liu, Shuting Pan, Hongxiang Zhang, Zifan Tang, Ji Liang, Yanyan Wang, Menglun Zhang, Xiaodong Hu, Wei Pang, and Xuexin Duan "A Universal Biomolecular Concentrator to Enhance Biomolecular Surface Binding Based on Acoustic NEMS Resonator" ACS Cent. Sci. 2018, 4, 899-908.
Ghulam Destgeer and Hyung Jin Sung "Recent advances in microfluidic actuation and micro-object manipulation via surface acoustic waves" Lab Chip, 2015, 15, 2722.
Rocío Bolaños-Jiménez, Massimiliano Rossi, David Fernandez Rivas, Christian J. Kähler and Alvaro Marin "Streaming flow by oscillating bubbles: quantitative diagnostics via particle tracking velocimetry" J. Fluid Mech. (2017), vol. 820, pp. 529-548.
Elena Igualada-Villodre, Ana Medina-Palomo, Patricia Vega-Martinez and Javier Rodriguez-Rodriguez "Transient effects in the translation of bubbles insonated with acoustic pulses of finite duration" J. Fluid Mech. (2018), vol. 836, pp. 649-693.
Long Meng, Feiyan Cai, Juanjuan Chen, Lili Niu, Yanming Li, Junru Wu, and Hairong Zheng "Precise and programmable manipulation of microbubbles by two-dimensional standing surface acoustic waves" Appl. Phys. Lett. 100, 173701 (2012).
Long Meng, Feiyan Cai, Zidong Zhang, Lili Niu, Qiaofeng Jin, Fei Yan, Junru Wu, Zhanhui Wang, and Hairong Zheng, "Transportation of single cell and microbubbles by phase-shift introduced to standing leaky surface acoustic waves" Biomicrofluidics 5, 044104 (2011).
Daniel Ahmed, Adem Ozcelik, Nagagireesh Bojanala, Nitesh Nama, Awani Upadhyay, Yuchao Chen, Wendy Hanna-Rose & Tony Jun Huang, "Rotational manipulation of single cells and organisms using acoustic waves" Nature Communications vol. 7, Article No. 11085 (2016).
Helen Mulvana, Sandy Cochran, Martyn Hill "Ultrasound assisted particle and cell manipulation on-chip" Advanced Drug Delivery Reviews vol. 65, Issues 11-12, Nov. 15, 2013, pp. 1600-1610.
Yu-Ren Liou, Yu-Hsin Wang, Chia-Ying Lee, Pai-Chi Li "Buoyancy-Activated Cell Sorting Using Targeted Biotinylated Albumin Microbubbles" PLoS ONE 10(5): e0125036, (May 20, 2015).
Yoshiki Yamakoshi, Naritsugu Nakajima and Takashi Miwa "Microbubble Trapping by Nonlinear Bubble Oscillation Using Pumping Wave" Japanese Journal of Applied Physics, vol. 46, Part 1, No. 7B, (2007).
Satya V.V.N. Kothapalli, Martin Wiklund, Birgitta Janerot-Sjoberg, Gaio Paradossi, Dmitry Grishenkov "Investigation of polymer-shelled microbubble motions in acoustophoresis" Ultrasonics vol. 70, Aug. 2016, pp. 275-283.
J.J. Rychak, A.L. Klibanov, J.A. Hossack "Acoustic radiation force enhances targeted delivery of ultrasound contrast microbubbles: in vitro verification" IEEE Transactions on Ultrasonics, Ferroelectrics, and Frequency Control, vol. 52, No. 3, Mar. 2005.
Ivo Leibacher, Philipp Hahn, Jürg Dual "Acoustophoretic cell and particle trapping on microfluidic sharp edges" Microfluidics and Nanofluidics Oct. 2015, vol. 19, Issue 4, pp. 923-933.
Kevin Cushing, Eva Undvall, Yvonne Ceder, Hans Lilja, Thomas Laurell "Reducing WBC background in cancer cell separation products by negative acoustic contrast particle immuno-acoustophoresis" Analytica Chimica Acta vol. 1000, Feb. 13, 2018, pp. 256-264.
Per Augustsson, Jonas T. Karlsen, Hao-Wei Su, Henrik Bruus & Joel Voldman, "Iso-acoustic focusing of cells for size-insensitive acousto-mechanical phenotyping" Nature Communications 7, Article No. 11556 (2016).
Ramachandraiah, Harisha "Microfluidic based isolation of circulating tumor cells from whole blood for cancer diagnostics" KTH, School of Biotechnology (BIO), Proteomics and Nanobiotechnology Doctoral Thesis Apr. 13, 2017.
Faridi, M. A., Ramachandraiah, H., Iranmanesh, I. S., Grishenkov, M.Wiklund, A. Russom "Microbubble assisted cell sorting by acoustophoresis" 20th International Conference on Miniaturized Systems for Chemistry and Life Sciences, MicroTAS 2016, Chemical and Biological Microsystems Society, 2016, p. 1677-1678.
Allen et al., "Dynamics of Therapeutic Ultrasound Contrast Agents", Ultrasound in Med. & Biol., vol. 28, No. 6, 2002, pp. 805-816.
Barber et al., "Light Scattering Measurements of the Repetitive Supersonic Implosion of a Sonoluminescing Bubble", Physical Review Letters, vol. 69, No. 26, Dec. 28, 1992, pp. 3839-3842.
Chen et al., "The Disappearance of Ultrasound Contrast Bubbles: Observations of Bubble Dissolution and Cavitation Nucleation", Ultrasound in Med & Biol., vol. 28, No. 6, 2002, pp. 793-803.
Dayton et al., "Optical and Acoustical Observations of the Effects of Ultrasound on Contrast Agents", IEEE Transactions on Ultrasonics, Ferroelectrics, and Frequency Control, vol. 46, No. 1, Jan. 1999, pp. 220-232.
De Jong et al., "Higher harmonics of vibrating gas-filled microspheres. Part one: simulations", Ultrasonics, vol. 32, No. 6, 1994, pp. 447-453.
De Jeong et al., "Higher harmonics of vibrating gas-filled microspheres. Part Two: measurements", Ultrasonics, vol. 32, No. 6, 1994, pp. 455-459.
De Jong et al., "Ultrasound scattering properties of Albunex microspheres", Ultrasonics vol. 31, No. 3, 1993, pp. 175-181.
Forsberg et al., "Effect of Filling Gases on the Backscatter from Contrast Microbubbles: Theory and in vivo Measurements", Ultrasound in Med. & Biol., vol. 25, No. 8, 1999, pp. 1203-1211.
Guan et al., "Using light scattering to measure the response of individual ultrasound contrast microbubbles subjected to pulsed ultrasound in vitro", J. Acoust. Soc. Am., vol. 116, No. 5, Nov. 2004, pp. 2832-2842.
Hansen, "Mie scattering as a technique for the sizing of air bubbles", Applied Optics, vol. 24, No. 19, Oct. 1, 1985, pp. 3214-3220.
Holt et al., "Mie scattering used to determine spherical bubble oscillations", Applied Optics, vol. 29, No. 28, Oct. 1, 1990, pp. 4182-4191.
Khismatullin et al., "Radial oscillations of encapsulated microbubbles in viscoelastic liquids", Physics of Fluids, vol. 14, No. 10, Sep. 2002, pp. 3534-3557.
Langley et al., "Critical-angle scattering of laser light from bubbles in water: measurements, models, and application to sizing of bubbles", Applied Optics, vol. 23, No. 7, Apr. 1, 1984, pp. 1044-1054.
Marsh et al., "Broadband Measurement of the Scattering-to-Attenuation Ration for Albunex© at 37° C.", Ultrasound in Med. & Biol., vol. 25, No. 8, 1999, pp. 1321-1324.
Marston et al., "Scattering of light by a coated bubble in water near the critical and Brewster scattering angles", SPIE vol. 925, Ocean Optics IX, 1988, pp. 308-316.
Moran et al., "Quantification of Microbubble Destruction of Three Fluorocarbon-Filled Ultrasonic Contrast Agents", Ultrasound in Med. & Biol., vol. 26, No. 4, 2000, pp. 629-639.
Morgan et al., "Experimental and Theoretical Evaluation of Microbubble Behavior: Effect of Transmitted Phase and Bubble Size", IEEE

(56) References Cited

OTHER PUBLICATIONS

Transactions on Ultrasonics, Ferroelectrics, and Frequence Control, vol. 47, No. 6, Nov. 2000, pp. 1494-1509.
Petersson et al., "Continuous separation of lipid particles from erythrocytes by means of laminar flow and acoustic standing wave forces", Lab Chip, 5, 2005, pp. 20-22.
Postema et al., "Ultrasound-Induced Encapsulated Microbubble Phenomena", Ultrasound in Med. & Biol., vol. 30, No. 6, 2004, pp. 827-840.
Sboros et al., "Understanding the limitations of ultrasonic backscatter measurements from microbubble populations", Physics in Medicine and Biology 47, 2002, pp. 4287-4299.
Shi et al., "Ultrasonic Characterization of the Nonlinear Properties of Contrast Microbubbles", Ultrasound in Med. & Biol., vol. 26, No. 1, 2000, pp. 93-104.
Tinkov, Steliyan et al, "New doxorubicin-loaded phospholipid microbubbles for targeted tumor therapy: in-vivo characterization", Sep. 22, 2010, Journal of Controlled Release, 148, 368-372.
Villanueva, Flordeliza S. et al., "Microbubbles Targeted to Intercellular Adhesion Molecule-1 Bind to Activated Coronary Artery Endothelial Cells", Jul. 7, 1998, American Heart Association, 98, 1-5.
Wolfrum et al., "Observations of pressure-wave-excited contrast agent bubbles in the vicinity of cells", Applied Physics Letters, vol. 81, No. 26, Dec. 23, 2002, pp. 5060-5062.
Zhang et al., "The Experimental Investigation of Ultrasonic Properties for a Sonicated Contrast Agent and Its Application in Biomedicine", Ultrasound in Med. & Biol, vol. 26, No. 2, 2000, pp. 347-351.
M. H. Julius, T. Masuda, and L. A. Herzenberg, "Demonstration that antigen-binding cells are precursors of antibody-producing cells after purification with a fluorescence-activated cell sorter," Proc. Nat. Acad. Sci. U.S.A. 69, 1934-1938 (1972).
S. Miltenyi, W. Müller, W. Weichel, and A. Radbruch, "High gradient magnetic cell separation with MACS," Cytometry 11, 231-238(1990).
P. J. Amos, E. Cagavi Bozkulak, and Y. Qyang, "Methods of cell purification: A critical juncture for laboratory research and translational science," Cells Tissues Organs 195, 26-40 (2012).
W. T. Coakley, D. W. Bardsley, M. A. Grundy, F. Zamani, and D. J. Clarke, "Cell manipulation in ultrasonic standing wave fields," J. Chem. Technol. Biot 44, 43-62 (1989).
W. T. Coakley, "Ultrasonic separations in analytical biotechnology," Trends Biotechnol. 15, 506-511 (1997).
J. J. Hawkes and W. T. Coakley, "Force field particle filter, combining ultrasound standing waves and laminar flow," Sens. Actuators, B 75, 213-222 (2001).
F. Petersson, A. Nilsson, C. Holm, H. Jönsson, and T. Laurell, "Separation of lipids from blood utilizing ultrasonic standing waves in microfluidic channels," Analyst 129, 938-943 (2004).
T. Laurell, F. Petersson, and A. Nilsson, "Chip integrated strategies for acoustic separation and manipulation of cells and particles," Chem. Soc. Rev. 36, 492-506 (2007).
M. Antfolk, C. Magnusson, P. Augustsson, H. Lilja, and T. Laurell, "Acoustofluidic, label-free separation and simultaneous concentration of rare tumor cells from white blood cells," Anal. Chem. 87, 9322-9328 (2015).
G. Goddard and G. Kaduchak, "Ultrasonic particle concentration in a line-driven cylindrical tube," J. Acoust. Soc. Am. 117, 3440-3447 (2005).
G. Goddard, J. C. Martin, S. W. Graves, and G. Kaduchak, "Ultrasonic particle-concentration for sheathless focusing of particles for analysis in a flow cytometer," Cytometry, Part A 69a, 66-74 (2006).
G. Kaduchak and M. D. Ward, "Application of acoustic radiation pressure to align cells in a commercial flow cytometer," Proc. Mtgs. Acoust. 19, 045014 (2013).
L. V. King, "On the acoustic radiation pressure on spheres," Proc. R. Soc. London, Ser. A 147, 212-240 (1934).
T. Segers and M. Versluis, "Acoustic bubble sorting for ultrasound contrast agent enrichment," Lab Chip 14, 1705-1714 (2014).
C. H. Hsu, C. C. Chen, D. Irimia, and M. Toner, "Isolating cells from blood using buoyancy activated cell sorting (BAGS) with glass microbubbles," in 14th International Conference on Miniaturized Systems for Chemistry and Life Sciences, edited by S. Verpoorte (Chemical and Biological Microsystems Society Groningen, The Netherlands, 2010).
M. A. Faridi, H. Ramachandraiah, I. Iranmanesh, D. Grishenkov, M. Wiklund, and A. Russom, "MicroBubble activated acoustic cell sorting," Biomed. Microdevices 19, 23-30 (2017).
L. P. Gor'kov, "On the forces acting on a small particle in an acoustical field in an ideal fluid," Sov. Phys. Dokl. 6, 773-775 (1962).
D. Hartono, Y. Liu, P. L. Tan, X. Y. S. Then, L. Y. L. Yung, and K. M. Lim, "On-chip measurements of cell compressibility via acoustic radiation," Lab Chip 11, 4072-4080 (2011).
A. Doinikov, "Bjerknes forces and translational bubble dynamics," in Bubble and Particle Dynamics in Acoustic Fields: Modern Trends and Applications, edited by A. Doinikov (Research Signpost, Kerala, India, 2005), pp. 1-49.
C. C. Church, "The effects of an elastic solid-surface layer on the radial pulsations of gas-bubbles," J. Acoust. Soc. Am. 97, 1510-1521 (1995).
L. Hoff, P. C. Sontum, and J. M. Hovem, "Oscillations of polymeric microbubbles: Effect of the encapsulating shell," J. Acoust. Soc. Am. 107, 2272-2280 (2000).
D. Chatterjee and K. Sarkar, "A Newtonian rheological model for the interface of microbubble contrast agents," Ultrasound Med. Biol. 29, 1749-1757 (2003).
P. Marmottant, S. van der Meer, M. Emmer, M. Versluis, N. de Jong, S. Hilgenfeldt, and D. Lohse, "A model for large amplitude oscillations of coated bubbles accounting for buckling and rupture," J. Acoust. Soc. Am. 118, 3499-3505 (2005).
L. D. Landau and E. M. Lifshitz, Fluid Mechanics, 2nd ed.: vol. 6 (Course of Theoretical Physics) (Pergamon Press, Oxford, 1987).
A. J. Reddy and A. J. Szeri, "Coupled dynamics of translation and collapse of acoustically driven microbubbles," J. Acoust. Soc, Am. 112, 1346-1352 (2002).
T. J. Matula, "Bubble levitation and translation under single-bubble sonoluminescence conditions," J. Acoust. Soc. Am. 114, 775-781 (2003).
Y. A. Kobelev and L. A. Ostrovskii, "Acoustic electrostatic analogy and the interaction of gas-bubbles in a liquid," Sov. Phys. Acoust. 30, 427-428 (1984).
S. Y. Emelianov, M. F. Hamilton, Y. A. Ilinskii, and E. A. Zabolotskaya, "Nonlinear dynamics of a gas bubble in an incompressible elastic medium," J Acoust. Soc Am. 115, 581-588 (2004).
N. Guz, M. Dokukin, V. Kalaparthi, and I. Sokolov, "If cell mechanics can be described by elastic modulus: Study of different models and probes used in indentation experiments," Biophys J. 107, 564-575 (2014).
Y. A. Kobelev and L. A. Ostrovsky, "Nonlinear acoustic phenomena due to bubble drift in a gas-liquid mixture," J. Acoust. Soc. Am. 85, 621-629 (1989).
C. Béguin, É. Pelletier, S. Étienne, E, "Void fraction influence on added mass in a bubbly flow," Eur. J. Mech. B—Fluid 56, 28-45 (2016).
L. A. Crum, "Bjerknes forces on bubbles in a stationary sound field," J. Acoust. Soc. Am. 57, 1363-1370 (1975).
S. M. van der Meer, B. Dollet, M. M. Voormolen, C. T. Chin, A. Bouakaz, N. de Jong, M. Versluis, and D. Lohse, "Microbubble spectroscopy of ultrasound contrast agents," J. Acoust. Soc. Am. 121, 648-656 (2007).
Thomas J. Matula, Oleg A. Sapozhnikov, Lev A. Ostrovsky, Andrew A. Brayman, John Kucewicz, Brian E. MacConaghy, and Dino De Raad, "Ultrasound-based cell sorting with microbubbles: A feasibility study" J. Acoust. Soc. Am. 144(1), Jul. 2018.
Verheul HMW, Pinedo HM. Clinical implications of drug resistance. In: Herbert M. Pinedo, editor. Drug Resistance in the Treatment of Cancer: Cambridge University Press; 1998. p. 199-231.
Saunders NA, Simpson F, Thompson EW, Hill MM, Endo-Munoz L, Leggatt G, Minchin RF, Guminski A. Role of intratumoural

(56) References Cited

OTHER PUBLICATIONS heterogeneity in cancer drug resistance: molecular and clinical perspectives. EMBO Mol Med. 2012;4(8):675-84. PMID: 22733553. PMCID: PMC3494067.

Schmitt MW, Loeb LA, Salk JJ. The influence of subclonal resistance mutations on targeted cancer therapy. Nat Rev Clin Oncol. 2016;13(6):335-47. PMID: 26483300. PMCID: PMC4838548.

Meacham CE, Morrison SJ. Tumour heterogeneity and cancer cell plasticity. Nature. 2013;501(7467):328-37. PMID 24048065. PMCID: PMC4521623.

Kaspers GJ, Veerman AJ, Pieters R, Van Zantwijk CH, Smets LA, Van Wering ER, Van Der Does-Van Den Berg A. In vitro cellular drug resistance and prognosis in newly diagnosed childhood acute lymphoblastic leukemia. Blood. 1997;90(7):2723-9. PMID: 9326239.

Volm M, Efferth T. Prediction of Cancer Drug Resistance and Implications for Personalized Medicine. Front Oncol. 2015;5:282 PMID: 26734568. PMCID: PMC4681783.

Unger FT, Witte I, David KA. Prediction of individual response to anticancer therapy: historical and future perspectives. Cell Mol Life Sci. 2015 ;72(4):729-57. PMID: 25387856. PMCID: PMC4309902.

Kaufmann SH, Earnshaw WC. Induction of apoptosis by cancer chemotherapy. Exp Cell Res. 2000;256(1):42-9. PMID: 10739650.

Martin SJ, Reutelingsperger CP, McGahon AJ, Rader JA, van Schie RC, LaFace DM, Green DR. Early redistribution of plasma membrane phosphatidylserine is a general feature of apoptosis regardless of the initiating stimulus: inhibition by overexpression of Bcl-2 and Abl. J Exp Med. 1995;182(5):1545-56. PMID: 7595224. PMCID: PMC2192182.

Vermes I, Haanen C, Steffens-Nakken H, Reutelingsperger C. A novel assay for apoptosis. Flow cytometric detection of phosphatidylserine expression on early apoptotic cells using fluorescein labelled Annexin V. J Immunol Methods. 1995;184(1):39-51. PMID: 7622868.

Riccardi C, Nicoletti I. Analysis of apoptosis by propidium iodide staining and flow cytometry. Nat Protoc. 2006;1(3):1458-61. PMID: 17406435.

Dayton P, Klibanov A, Brandenburger G, Ferrara K. Acoustic radiation force in vivo: a mechanism to assist targeting of microbubbles. Ultrasound Med Biol. 1999;25(8):1195-201. PMID: 10576262.

Elmore S. Apoptosis: a review of programmed cell death. Toxicol Pathol. 2007;35(4):495-516. PMID: 17562483. PMCID: PMC2117903.

Garraway LA, Janne PA. Circumventing cancer drug resistance in the era of personalized medicine. Cancer Discov. 2012;2(3):214-26. PMID: 22585993.

Lewis RE, Cruse JM, Sanders CM, Webb RN, Suggs JL. Aberrant expression of T-cell markers in acute myeloid leukemia. Exp Mol Pathol. 2007;83(3):462-3. PMID: 17927977.

Turajlic S, Furney SJ, Stamp G, Rana S, Ricken G, Oduko Y, Saturno G, Springer C, Hayes A, Gore M, Larkin J, Marais R. Whole-genome sequencing reveals complex mechanisms of intrinsic resistance to BRAF inhibition. Ann Oncol. 2014;25(5):959-67. PMID: 24504448. PMCID: PMC3999800.

\* cited by examiner

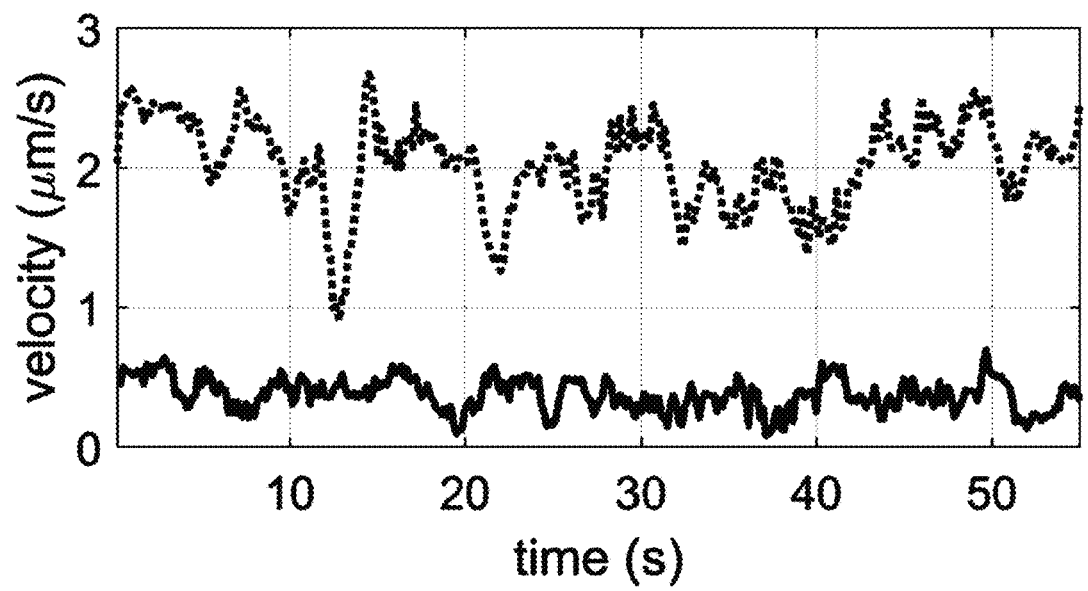
FIG. 12B
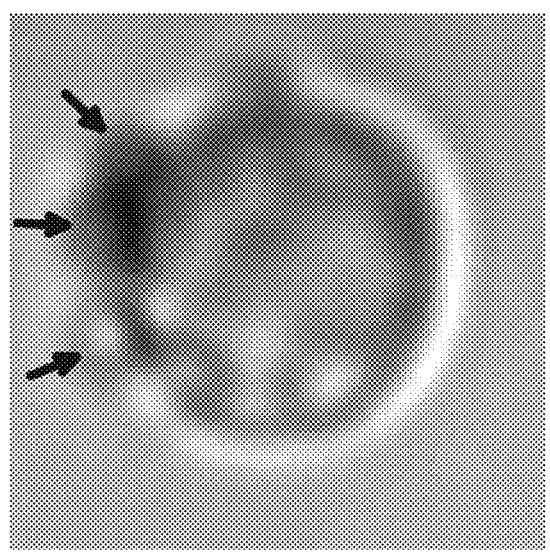 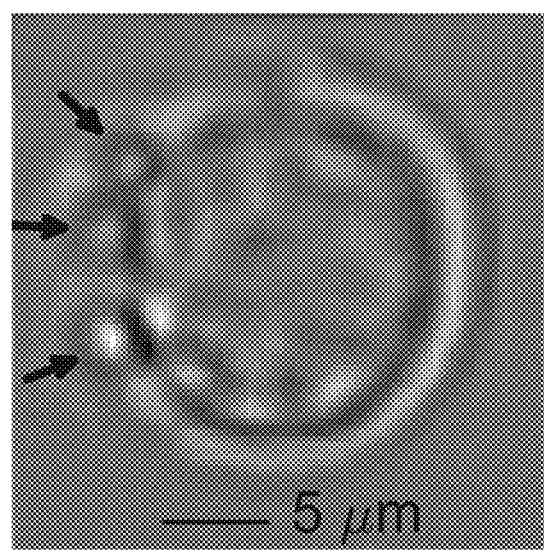
FIG. 13A          FIG. 13B

REAL-TIME CELL-SURFACE MARKER DETECTION

CROSS-REFERENCE TO RELATED APPLICATION

This application claims the benefit of U.S. Provisional Application No. 62/690,452, filed Jun. 27, 2018, which is incorporated herein by reference in its entirety.

STATEMENT OF GOVERNMENT LICENSE RIGHTS

This invention was made with government support under Grant No. P01 DK043881, awarded by the National Institutes of Health. The Government has certain rights in the invention.

BACKGROUND

The isolation and sorting of cells is an important process in research and hospital labs. Cell therapies (e.g., cell-based immunotherapies, stem cells) require the isolation and/or purification of cells. Most large research and commercial labs incorporate fluorescently or magnetically labeled antibodies adherent to cell surface antigens for cell identification and separation. Unique cluster of differentiation (CD) cell surface antigens are some of the markers that can be exploited for highly selective labeling and thus, isolation and purification.

Standard cell separation technologies that use cell surface antigens include fluorescently activated cell sorters (FACS), which rely on fluorescent particle labeling, or magnetically activated cell sorters (MACS), which rely on magnetic particle labeling. FACS allows for separation based on several markers, but requires relatively large sample volumes, and is not available in most small labs because of cost. Magnetic bead sorting is less expensive, but there are fewer antibodies available for conjugation, and enzymatic digestion is needed to remove the magnetic particles.

Ultrasound-based cell separation has emerged as a new separation strategy in which cells are separated by utilizing standing ultrasound waves. Under these conditions, cells are attracted to, and align with, the pressure node. One example of a commercial application of this technology is the AttuneVR flow cytometer, which adds a standing acoustic wave to assist with the hydrodynamic focusing of cells. A motivation for using standing waves is that forces acting on particles can be much greater with standing waves than with traveling waves. An added advantage of these systems is that in some cases the separation can be performed label-free. The disadvantage to these acoustic label-free techniques is that there must be a relatively significant difference in density, compressibility, or morphology between the particles to efficiently separate them. Additionally, and because of the high-Q of standing waves, small changes in the environment, such as temperature, can affect performance of cell sorters utilizing standing waves.

Thus, a need still exists for a cell sorting system and methods that utilize acoustic waves without the drawbacks of the existing sorting systems.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a cell-sorting system comprising:

a flow cell for flowing a sample comprising microbubble-labeled cells and unlabeled cells, wherein the flow cell comprises one or more inlet channels, a flow channel having an upstream portion and a downstream portion, and one or more outlet channels; and one or more acoustic transducers acoustically coupled with the flow cell, wherein the one or more acoustic transducers is positioned and configured to deliver a traveling acoustic wave through the flow channel, wherein the traveling acoustic wave applies an acoustic radiation force to a sample flowing through the flow channel such that the microbubble-labeled cells are displaced relative to unlabeled cells.

In some embodiments, the cell-sorting system disclosed herein comprises a flow cell comprising a recirculating channel connecting the upstream portion and the downstream portion of the flow channel and configured to return the portion of the flow depleted of microbubble-labeled cells back into the flow cell. In some embodiments, the cell-sorting system can comprise two or more transducers which are configured to produce different frequencies such that when a sample comprising two or more populations of microbubble-labeled cells, wherein each population of microbubble-labeled cells is labeled with microbubbles of different size, is flowed through the flow channel, the two or populations of microbubble-labeled cells are separated from each other and the unlabeled cells.

In a second aspect, the disclosure provides a method for real-time monitoring of apoptosis in a population of cells comprising cells undergoing apoptosis comprising:

contacting a sample comprising a population of cells with microbubbles conjugated to an agent that binds to a cell-surface apoptosis marker to form a sample wherein at least a portion of cells undergoing apoptosis is labeled with microbubbles;

flowing the sample wherein at least a portion of cells undergoing apoptosis is labeled with microbubbles through a flow cell comprising one or more inlet channels, a flow channel having an upstream portion and a downstream portion, one or more outlet channels, and one or more acoustic transducers acoustically coupled with the flow cell, wherein the one or more acoustic transducers is positioned and configured to deliver a traveling acoustic wave through the flow channel; and applying an acoustic radiation force generated by the traveling acoustic wave to the sample flowing through the flow channel such that the microbubble-labeled cells are displaced relative to unlabeled cells.

In some embodiments, the cell-surface apoptosis marker is phosphatidylserine. In some embodiments, the agent that binds to the cell-surface apoptosis marker is Annexin V.

In a third aspect, provided herein is a method for screening for an apoptotic activity of a therapeutic agent comprising:

contacting a sample comprising a population of cell with a therapeutic agent;

contacting the sample contacted with the therapeutic agent with a microbubble conjugate of an agent that binds to a cell-surface apoptosis marker to form a sample wherein at least a portion of cells is labeled with microbubbles;

flowing the sample wherein at least a portion of cells is labeled with microbubbles through a flow cell comprising one or more inlet channels, a flow channel having an upstream portion and a downstream portion, one or more outlet channels, and one or more acoustic transducers acoustically coupled with the flow cell, wherein the one or more acoustic transducers is positioned and configured to deliver a traveling acoustic wave through the flow channel; and applying an acoustic radiation force generated by the traveling acoustic wave to the sample flowing through the flow channel such that the microbubble-labeled cells are displaced relative to unlabeled cells.

In some embodiments, the therapeutic agent is an investigational therapeutic agent not yet approved by a regulatory agency. In other embodiments, the therapeutic agent is a chemotherapeutic agent approved for treatment of malignancies.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 12B shows corresponding velocities of the two pairs in FIG. 12A. The smaller cell with 3 MBs (dashed line) moves 5× faster than the bigger cell with one attached MB (solid line).

FIG. 13A is an image of a leukemia cell with three attached MBs (shown by arrows). FIG. 13B is a filtered image which shows the three attached MBs. The cell image is a composite image of 20 frames during which time the cell was relatively stable as ultrasound was not on. Translational and rotational cross-correlation was used to align the image frames prior to averaging. The composite image was high-pass filtered using a Gaussian kernel. The average cell diameter was about 11±2 μm.

FIG. 16A depicts response of bubbles that are close in size, and FIG. 16B demonstrates that greater size difference allows greater separation. FIG. 16C illustrates that each cell moves maximally if the frequency is matched to the resonance bubble size.

DETAILED DESCRIPTION

Figure 1:
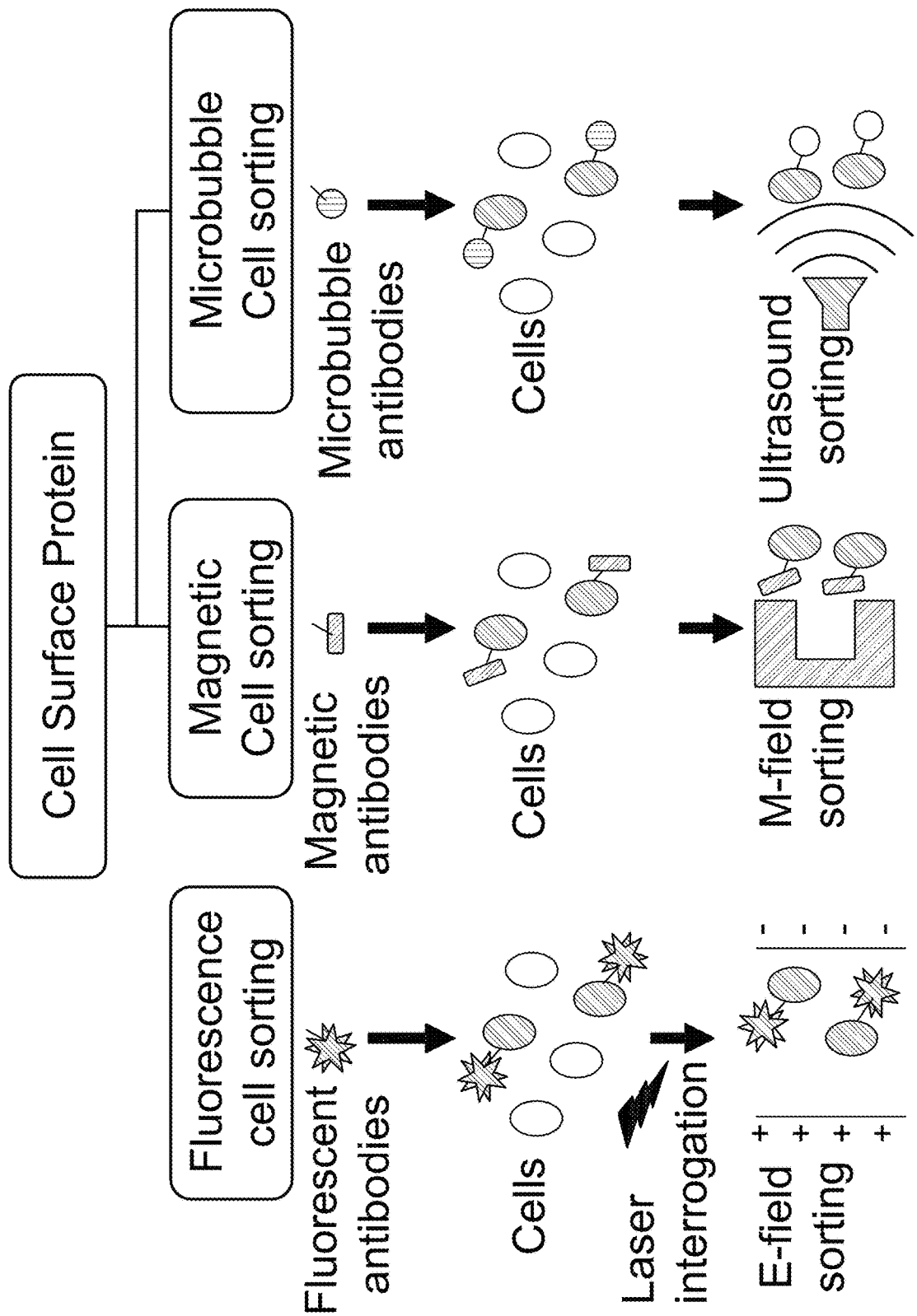
FIG. 1 is a schematic of cell purification methods based on cell surface antigen expression. Fluorescently-Activated Cell Sorters (FACS, left) rely on antibodies labeled with fluorophores to bind to cells, and then use electric fields to sort them. Magnetic cell sorters (middle) rely on antibodies labeled with magnetic particles to bind to cells, and magnetic fields to isolate them. The system of the present disclosure, a Microbubble Cell Sorter (MiCS, right) use antibodies labeled with microbubbles (MBs) to bind to cells and rely on ultrasound to sort them.

Disclosed herein is the use of ultrasound-based tags, namely, microbubbles (MBs), which are highly reactive to acoustic waves, to facilitate separation of cells using traveling waves. In contrast to standing waves, traveling waves allow sorting or isolating MB-labeled cells over a distance larger than half an acoustic wavelength and can provide greater performance stability. Thus, an ultrasound based sorter that utilizes traveling waves for cell enrichment and purification processes provides a high-throughput, inexpensive solution that can be economically scaled. Additional benefits of such a sorter include rare cell detection and isolation, as well as low sample volume sorting. Instead of relying on lasers and fluorophores (or magnets and magnetic particles), ultrasound transducers and MBs are used (FIG. 1). Cells can be incubated with MBs and appropriate intermediate ligands for binding, and once the MBs are conjugated to the cells, small amplitude ultrasound pulses can effectively displace the cell-MB conjugates relative to unbound or unconjugated cells.

Thus, in a first aspect, the disclosure provides a cell-sorting system comprising:

a flow cell for flowing a sample comprising microbubble-labeled cells and unlabeled cells, wherein the flow cell comprises an inlet, a flow channel having an upstream portion and a downstream portion, and at least one outlet; and one or more acoustic transducers acoustically coupled with the flow cell, wherein the one or more acoustic transducers is positioned and configured to deliver a traveling acoustic wave through the flow channel, wherein the traveling acoustic wave applies an acoustic radiation force to a sample flowing through the flow channel such that the microbubble-labeled cells are displaced relative to unlabeled cells.

The systems and methods of the disclosure use acoustic radiation force to separate microbubble-labeled cells from unlabeled cells. Generally, cells have intrinsic acoustic impedance very close to the fluids they are immersed in. With such a small difference, there is only a weak interaction between acoustic waves and cells. This weak interaction may make it difficult to sort cells with acoustics alone. Bubbles, on the other hand, interact very strongly with ultrasound, as their compliance and density differ by orders of magnitude from the surrounding fluid. Throughout this disclosure, the terms "bubbles" and "microbubbles" or MBs are used interchangeably. Accordingly, in some embodiments, microbubbles with specific ligands can be bound or otherwise attached to cells of interest. When the cells are exposed to acoustic fields, the bubble-cell conjugate or bubble-cell assembly can undergo volumetric changes due to the positive and negative stresses induced on the structure (showing up as a variable signal with the same rate of changes as the ultrasound frequency). The terms "bubble-cell assembly," "bubble-cell conjugate" and "bubble-tagged call" are used interchangeably throughout the disclosure and describe one or more microbubbles, reversibly or irreversibly, coupled to a cell surface.

Microbubbles and microbubble ligands are known in the art and are commercially available from the field of ultrasound contrast agents. Alternatively, liposomes, or nanoparticles, or other particles that have an acoustic impedance that differs from the surrounding media can be used in the systems and methods disclosed herein. Particles can be selected based in-part on their acoustic impedance properties. In some embodiments, it can advantageous to utilize particles with an acoustic impedance that is different from the surrounding media so that the particle will be sensitive to acoustic waves. Microbubbles (MBs) utilized as ultrasound contrast agent are relatively small (on the order of microns in size, e.g., 1 µm in diameter) bubbles including a shell and a core. Shells are generally implemented using lipids, polymers, and/or albumin and various other surface components, while cores are generally implemented using gases such as air, perfluoropropane (PFP), perfluorobutane (PFB), and octafluoropropane (OFP), or the like. While methods and systems are generally described as using bubbles, it should be understood that bubbles of other sizes may be used depending on the application. In some circumstances, larger bubbles can be used in the methods and systems disclosed herein. Thus, in certain embodiments, the MBs used herein have a diameter of about 1 µm, about 2 µm, about 3 µm, about 5 µm, about 7 µm, about 10 µm, about 15 µm, about 20 µm, about 25 µm, about 30 µm, about 40 µm, or about 50 µm. In certain embodiments, two or more conjugates of bubbles of different sizes can be used to differentiate and/or separate two or more cell populations as described below.

Figure 5:
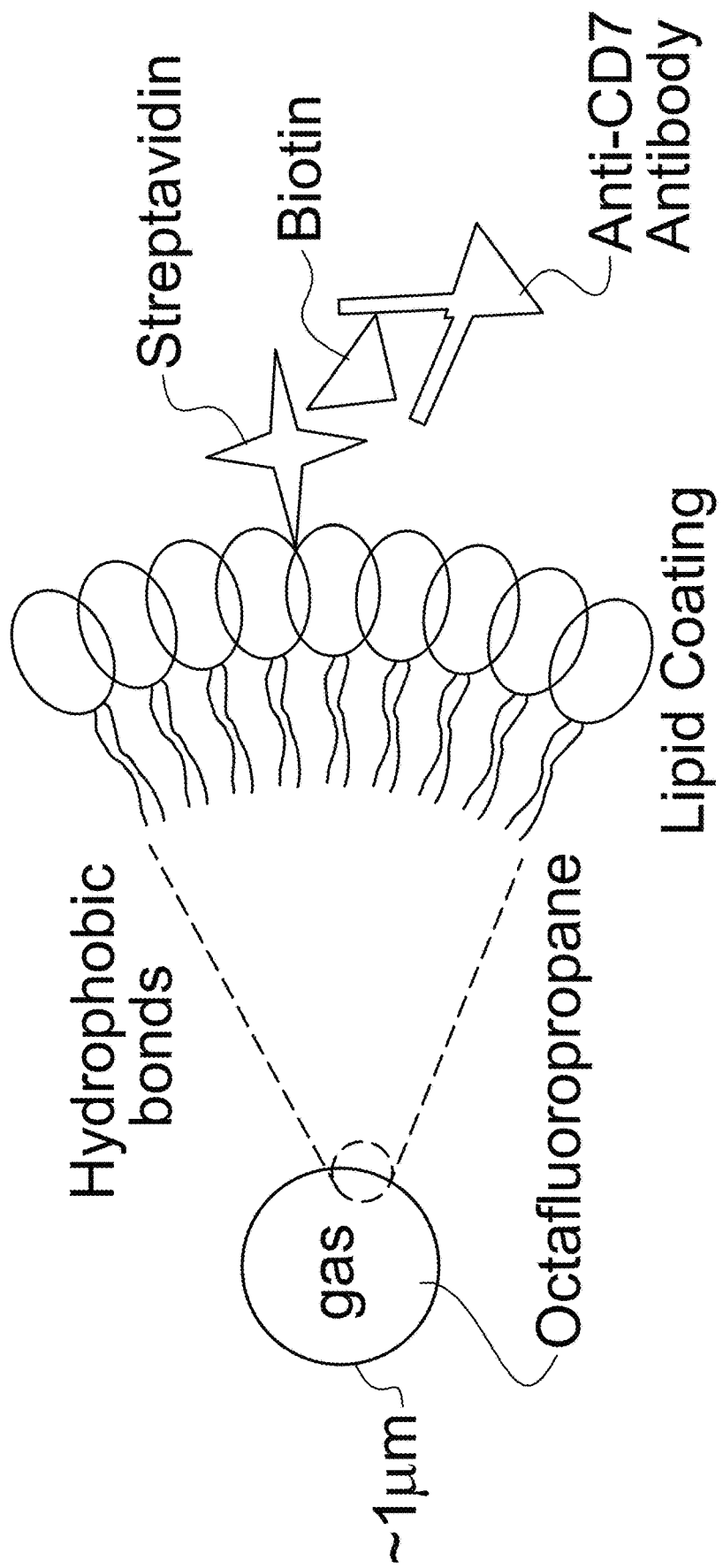
FIG. 5 is a schematic of a microbubble tagged to a leukemia CD7 antigen.

These bubbles can be attached to cells of interest using covalent or non-covalent binding strategies using linkages known in the art. For example, one of the most common linking strategies uses the avidin-biotin or streptavidin-biotin complexes. An exemplary labeling system including a streptavidin-labeled microbubble and a biotin-labeled cell-surface binding agent (e.g., anti-CD7 antibody) is shown in FIG. 5. An agent that specifically binds to a target molecule on the surface of a cell is bound to a ligand, e.g., biotin. Upon contacting with a streptavidin-labeled microbubble, the biotin conjugate forms a complex with the microbubble resulting in a microbubble that can specifically bind to the target molecule. Thus, cells that comprise that particular target molecule on the cell surface will form bubble-cell assemblies when contacted with such microbubble that can specifically bind to the target molecule. Cells without the specific target (e.g., antigen) won't be bound to the bubble. For example, cells express different proteins (antigens) on the cell surface, and the antigens present depend on the cell type. Accordingly, cells of interest can be differentiated or distinguished from a remainder of a cell sample by identifying specific antigens which are specific to the cells of interest. Antibodies which will bind the specific cell surface antigens can be prepared, and will only interact with cells expressing that specific antigen (i.e., the cells of interest). When using a biotin-avidin or biotin-streptavidin binding strategy, the method utilizes the strong binding between the biotin protein and avidin or streptavidin. If a specific antibody is labeled with biotin, the antibody can now bind to both the cell surface antigen against which it was raised, and also to other structures which possess biotin at their surfaces. These might include biotinylated bubble shells. It is by this or similar mechanism that bubbles may be modified so that they bind to only those cells which express the antigen.

Figure 4A:
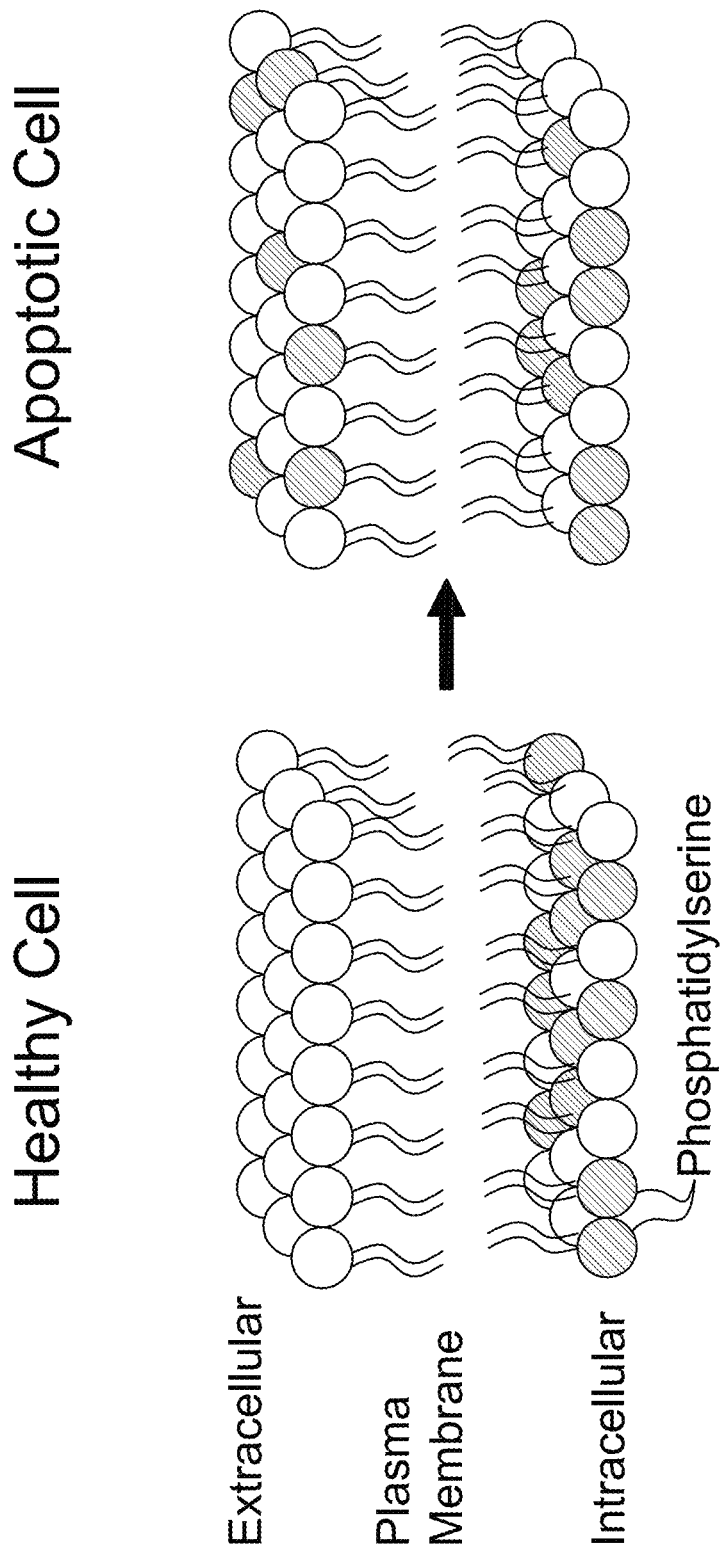
FIGS. 4A and 4B depict the membrane of a cell undergoing apoptosis. Phosphatidylserine (PS), normally located in the cell's inner cytoplasmic membrane surface, is translocated to the outer leaflet during early stages of apoptosis and signals macrophages to engulf the cells (4A). Microbubble-labeled Annexin V, a biomarker that binds to PS, can be used for microbubble-labeling of cells undergoing apoptosis (4B).
Figure 4B:
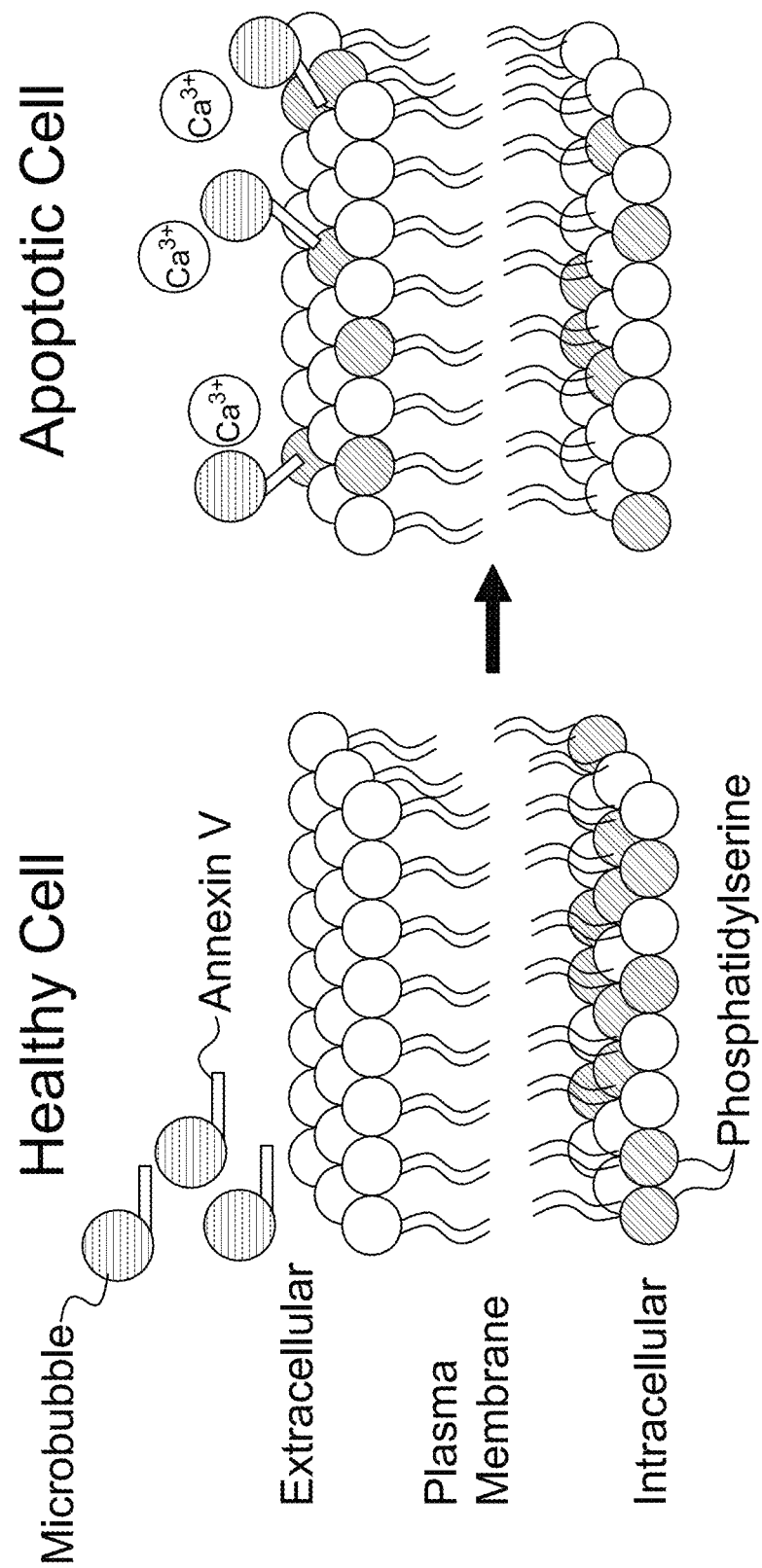

In some embodiments, the cell surface target molecule can be an apoptosis marker, for example, phosphatidylserine (PS). In normal cells, phosphatidylserine (PS) residues are found in the inner membrane of the cytoplasmic membrane. During apoptosis, the PS residues are translocated in the membrane and are externalized, as shown in FIGS. 4A and 4B. In general, this is an early event in apoptosis and is thought to be a signal to neighboring cells that a cell is ready to be phagocytosed. Annexin V is a specific PS-binding protein that can be used to detect apoptotic cells. Avidinated microbubbles, such as octafluoropropan-filled phospholipid can be conjugated with biotinylated annexin A5 (for example, according to the procedure described in Min P K, Lim S, Kang S J, et al. Targeted ultrasound imaging of apoptosis with annexin a5 microbubbles in acute Doxorubicin-induced cardiotoxicity. *J Cardiovasc Ultrasound.* 2010; 18(3):91-97). Annexin V has been used to quantitate the extent of apoptosis in cell populations, e.g., cell cultures. Based on their annexin V-affinity, resulting from phosphatidylserine (PS) exposure at the outer leaflet of the plasma membrane, apoptotic cells can be distinguished from annexin V-negative living cells that do not undergo apoptosis.

In some embodiments, the methods disclosed herein can use one or more other markers, for example, a marker used to detect necrosis, such as propidium iodide (PI). Such double labeling procedure can allow a further distinction of necrotic (annexin V+/PI+) and apoptotic (annexin V+/PI−) cells. In some embodiments, cells can be incubated with annexin V prior to harvesting and cells damaged during isolation procedures (annexin V−/PI+) can also be identified.

The systems and methods of the disclosure rely on subjecting the bubble-cell assembly to acoustic radiation forces causing displacement of the bubble-tagged cells. The systems and methods disclosed herein can detect the volumetric changes and/or displacements in order to differentiate some cells, e.g., bubble-tagged cells, from other cells in a cell sample.

In some embodiments, the acoustic wave is a traveling acoustic wave generated by an acoustic transducer. In some embodiments, the sample can be placed in a flow channel of a flow cell and the acoustic wave can be delivered generally transverse to the direction of sample flow. Embodiments of systems for cell sorting utilizing traveling waves are described in further details below.

Since bubbles have very strong interactions with acoustic waves, they are easily displaced in response to the acoustic wave. Cells of interest that are labeled with microbubbles will also be displaced and will move with the attached bubble. Cells without microbubbles, however, have very weak interactions with ultrasound and will move only slightly in response to the acoustic wave. Further, in some embodiments, cells with attached bubbles may be pushed in a different direction than an untagged cell. For example, when applying a standing wave to a cell sample, cells with attached bubbles and unassociated ("free") bubbles that are smaller than their resonant size are pushed toward pressure antinodes of the standing wave, whereas cells which are not bound to bubbles are pushed toward pressure nodes of the standing wave. In contrast, when a traveling wave is applied to a sample comprising microbubble-tagged cells, the traveling wave pushes the bubble along the propagation direction; i.e., away from the source. As the result, the cells are displaced relative to the cells that are not labeled with the bubbles. Unlike the case with standing waves, there are no restrictions on the size of the interaction zone. The largest zone in a standing wave system is about a half wavelength.

Figure 17:
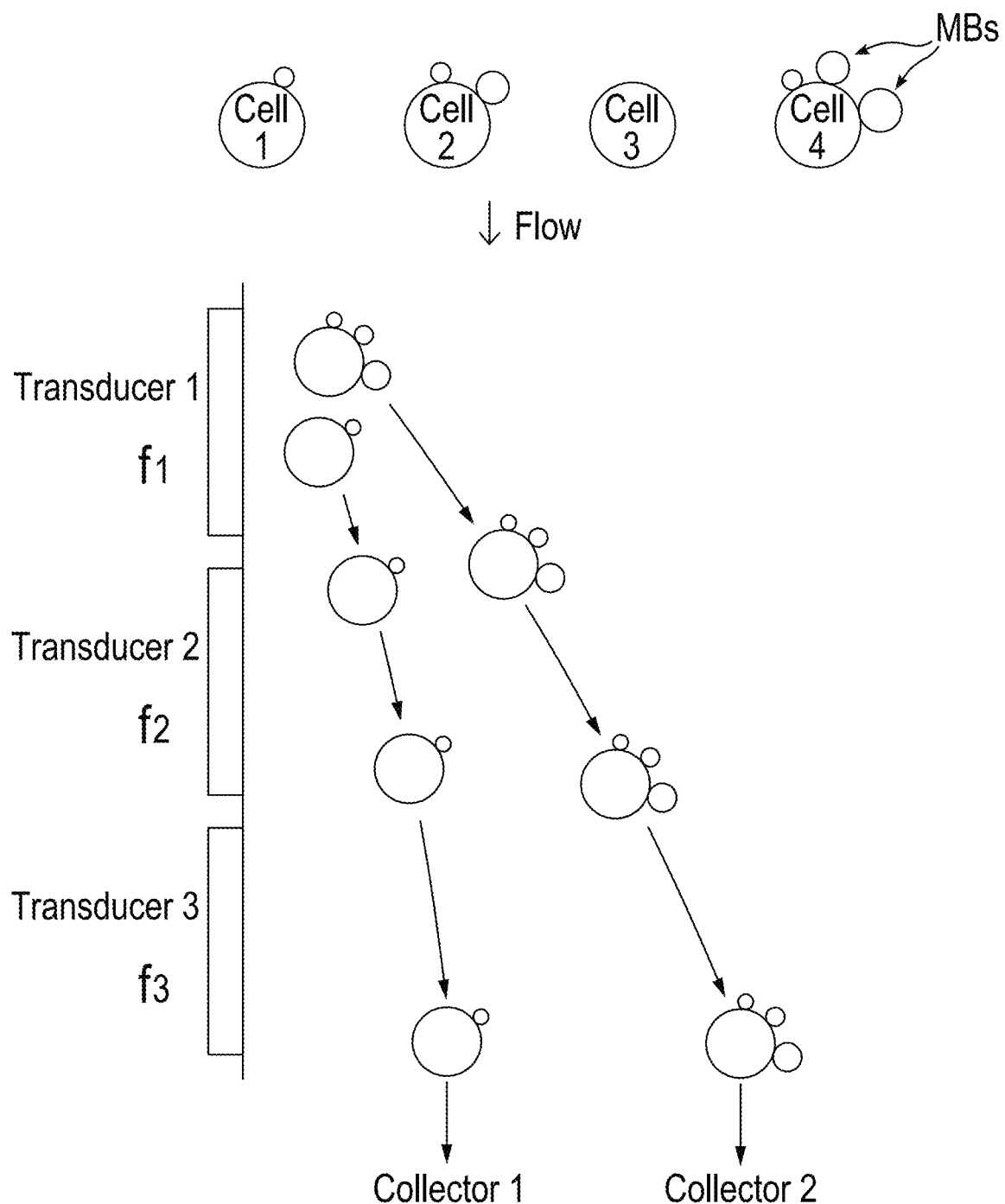
FIG. 17 is a schematic demonstrating sorting of cells based on several cell surface markers.

Also, the force in a traveling wave can be bigger than a standing wave when driven at resonance (FIG. 17). A standing wave structure only allows for discrete wavelengths (multiples of a half wavelength) to fit within the interaction zone. Finally, unlike traveling wave systems, a standing wave system would require an electronic feedback loop to maintain the resonance of the system.

In some embodiments, the acoustic radiation force of the traveling wave can displace microbubble-labeled cells by a distance greater than the displacement distance caused by standing wave. For example, in some embodiments, the microbubble-labeled cells can be displaced by at least about 0.1 mm relative to unlabeled cells. For example, in other embodiments, the microbubble-labeled cells can be displaced by at least about 0.2 mm, at least about 0.3 mm, at least about 0.4 mm, at least about 0.5 mm, at least about 1 mm, at least about 2 mm, at least about 5 mm, at least about 10 mm, or at least about 20 mm relative to unlabeled cells.

Accordingly, the bubble-tagged cells can be differentiated from a remainder of the cell sample based on differences in displacement in response to the acoustic wave.

Figure 2:
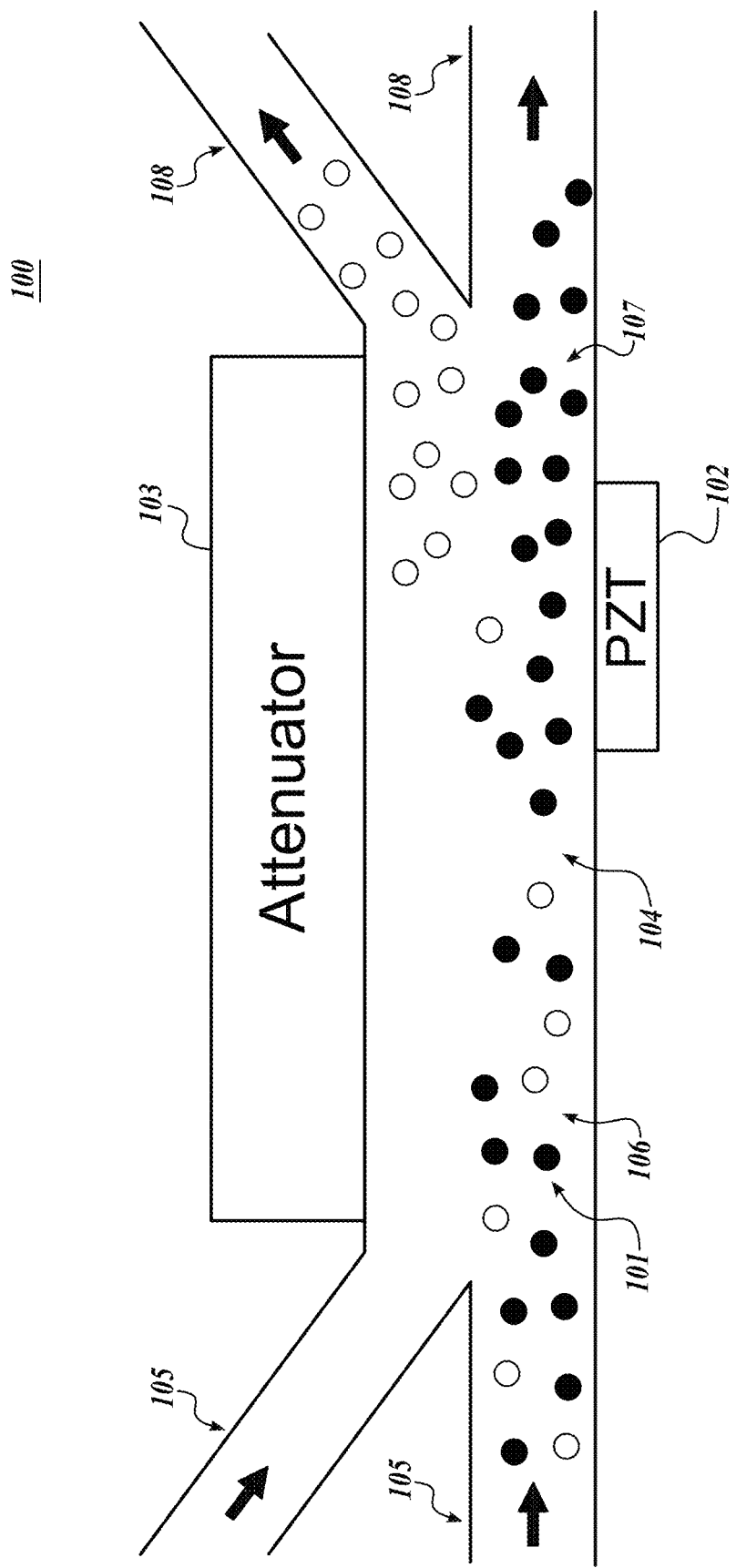
FIG. 2 depicts an exemplary system. The black circles represent unlabeled cells, and the white circles represent cells labeled with microbubbles or microbubbles that are not attached to cells.

FIG. 2 illustrates an exemplary cell sorting system 100. The system 100 comprises a flow cell 101 acoustically coupled to an acoustic source 102 for example, one or more acoustic transducers, and attenuator 103. The flow cell includes a flow channel 104 for flowing a sample through the flow cell. The one or more transducers 102 are configured to apply an acoustic radiation force to the cell sample as the cell sample flows through the flow channel 104. The attenuator 103 is positioned and configured to absorb the acoustic wave which has traveled through the flow channel preventing reflection. The flow cell further comprises one or more inlet channels 105, an upstream portion 106, a downstream portion 107, and one or more outlet channels 108, which can be used to collect cells of interest. In the system shown in FIG. 2, all cells, labeled and unlabeled, are flowed from the bottom inlet channel 105. Saline or another sheath liquid is flowed from the upper inlet channel 105. All the cells are kept in the bottom half of the interaction zone of the flow channel 104 until the ultrasound pushes the labeled cells upward into the upper flow of the outlet channel 108.

The transducers used in the systems and methods disclosed herein include a piezoelectric element, usually made of PZT-8 (lead zirconate titanate). Such elements may have an inch cross-section and a nominal 2 MHz resonance frequency, and can also be of a larger size. Each ultrasonic transducer module can have only one element, or can have multiple elements that each act as a separate ultrasonic transducer and are either controlled by one or multiple amplifiers. The piezoelectric element can be crystalline, semi-crystalline, or non-crystalline. The piezoelectric element can be square, rectangular, irregular polygon, or generally of any arbitrary shape.

In some embodiments, the cell-sorting system's downstream portion of the flow channel splits into two or more sub-channels or outlet channels 108 configured to separate the portion of the flow enriched in microbubble-labeled cells from the portion of the flow depleted of microbubble-labeled cells. In some embodiments, a portion of the sample comprising the displaced microbubble-labeled cells is collected, for example, into a reservoir configured as a cell collector. In some embodiments, the system can further comprise a disrupting chamber coupled with the outlet channel containing the portion of the sample enriched in microbubble-labeled cells or with the cell collector. In certain embodiments, the disrupting chamber is configured to create an overpressure or underpressure sufficient to rupture the microbubbles thus providing cells that do not comprise microbubbles associated with the cell surface. Overpressure may be an added static pressure to force the gas out of the bubbles, effectively destroying them. Underpressure can be a partial vacuum applied to force the bubbles to grow until they grow too big and break, thereby also destroying the bubbles. Varying (dynamic, or oscillatory) pressure, not just static pressure can also be used to destroy bubbles once the cells of interest have been concentrated.

Figure 16A:
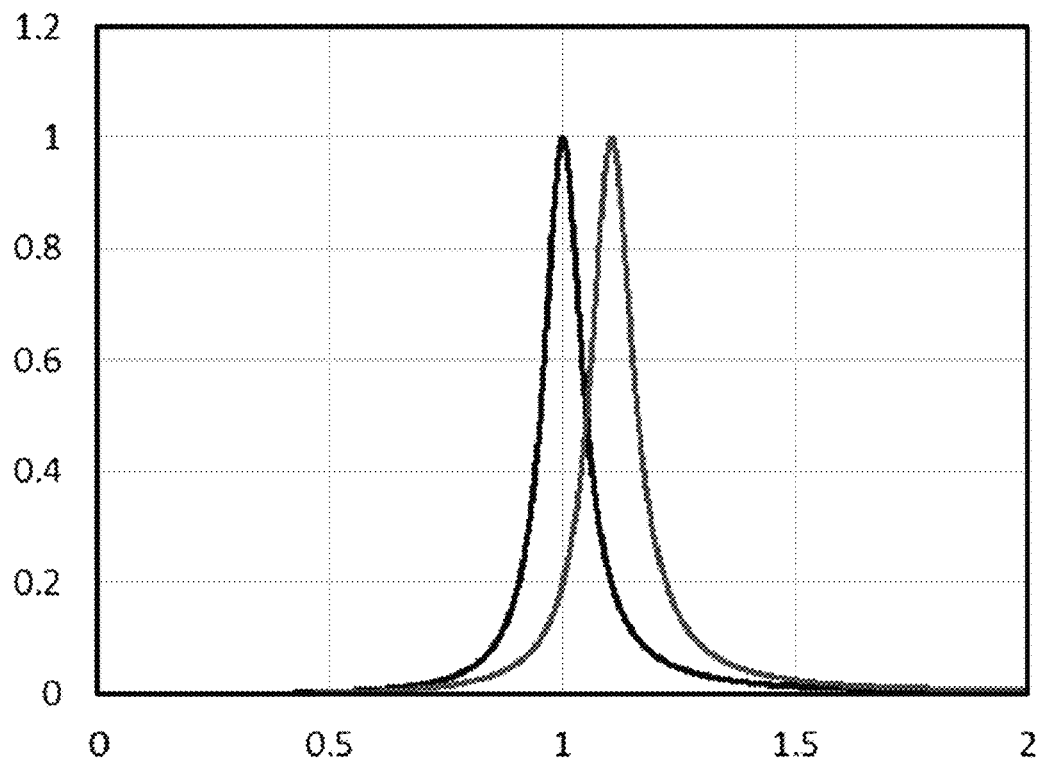
FIG. 16A-16C demonstrate that it is possible to separate two population of cells labeled with bubbles of different size.
Figure 16B:
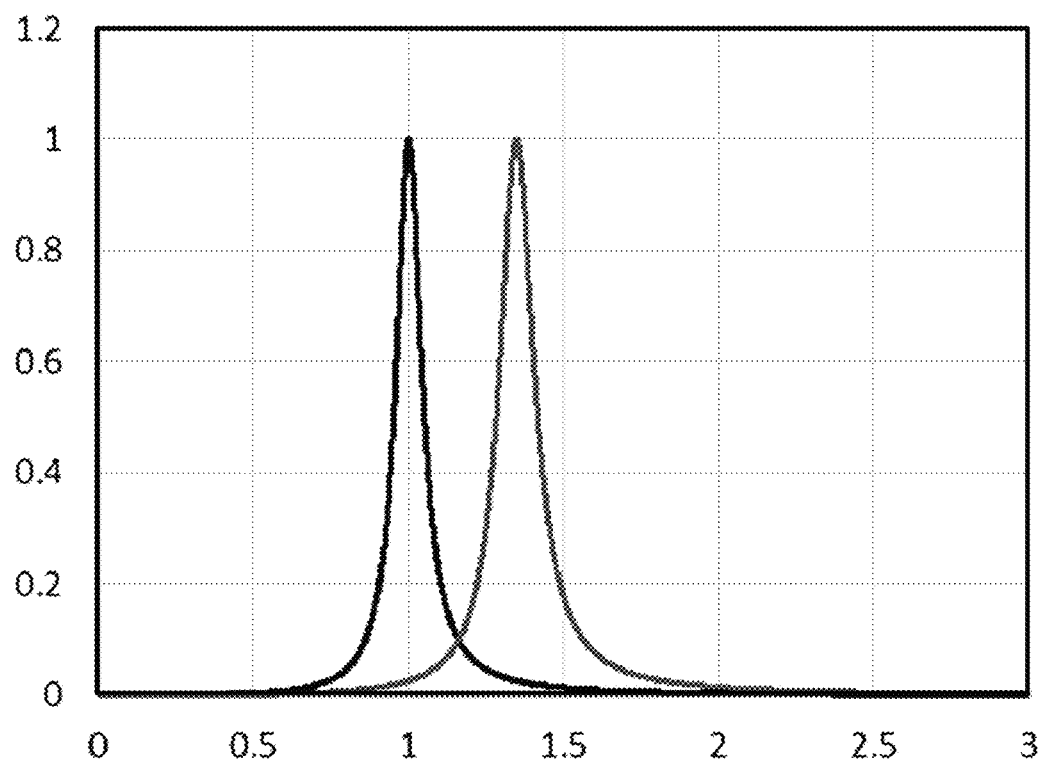
Figure 16C:
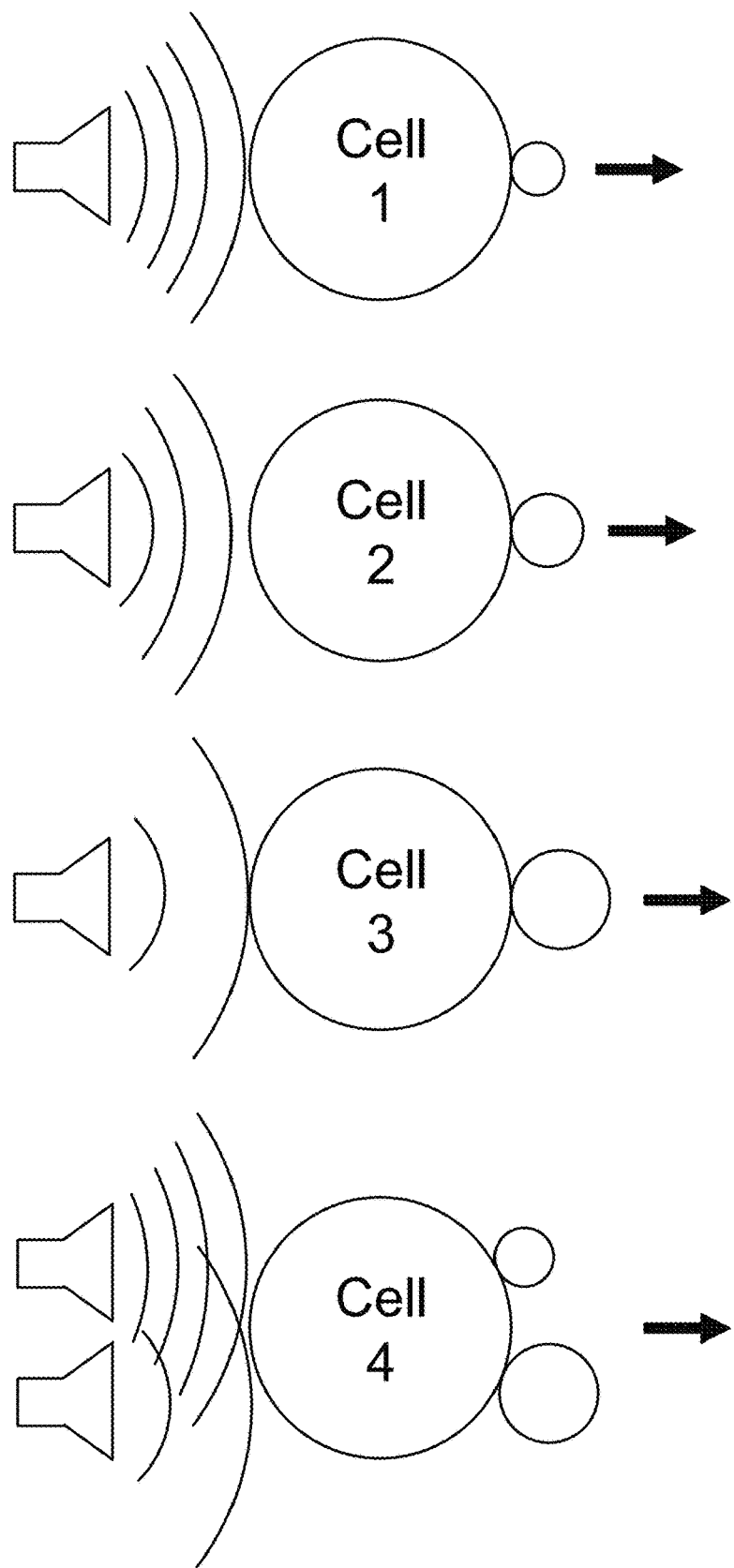

In some embodiments, the systems disclosed herein can comprise two or more transducers. The two or more transducers can be configured to produce different frequencies such that when a sample comprising two or more populations of microbubble-labeled cells, wherein each population of microbubble-labeled cells is labeled with microbubbles of different size, is flowed through the flow channel, the two or populations of microbubble-labeled cells are separated from each other and the unlabeled cells. FIGS. 16A-16C depict separation of cells labeled with MBs of different size, showing that each cell moves maximally if the frequency is matched to the resonance bubble size. When cells are being sorted based on two or more markers (e.g., dual-labeled Cell 4 of FIG. 16C), a dual-labeled cell would move (e.g., separate from mono-labeled cell Cell 1, Cell 2, or Cell 3) the fastest if the frequencies matched the resonance size of the two attached microbubbles. FIG. 17 illustrates movement of differentially labeled cells through a system with three transducers based on three microbubbles of different sizes designed to selectively bind to 3 cell markers. As a fully-labeled cell comprising all three markers flows downward, it is sequentially displaced by transducer 1, transducer 2, and transducer 3, each operating at a resonance frequency ($f_1$, $f_2$, and $f_3$) of one of the bubbles. Another cell, for example, a cell with only one bubble attached, is also displaced, but by a lesser distance, thus allowing the separation distance to isolate the different populations of cells.

Figure 3:
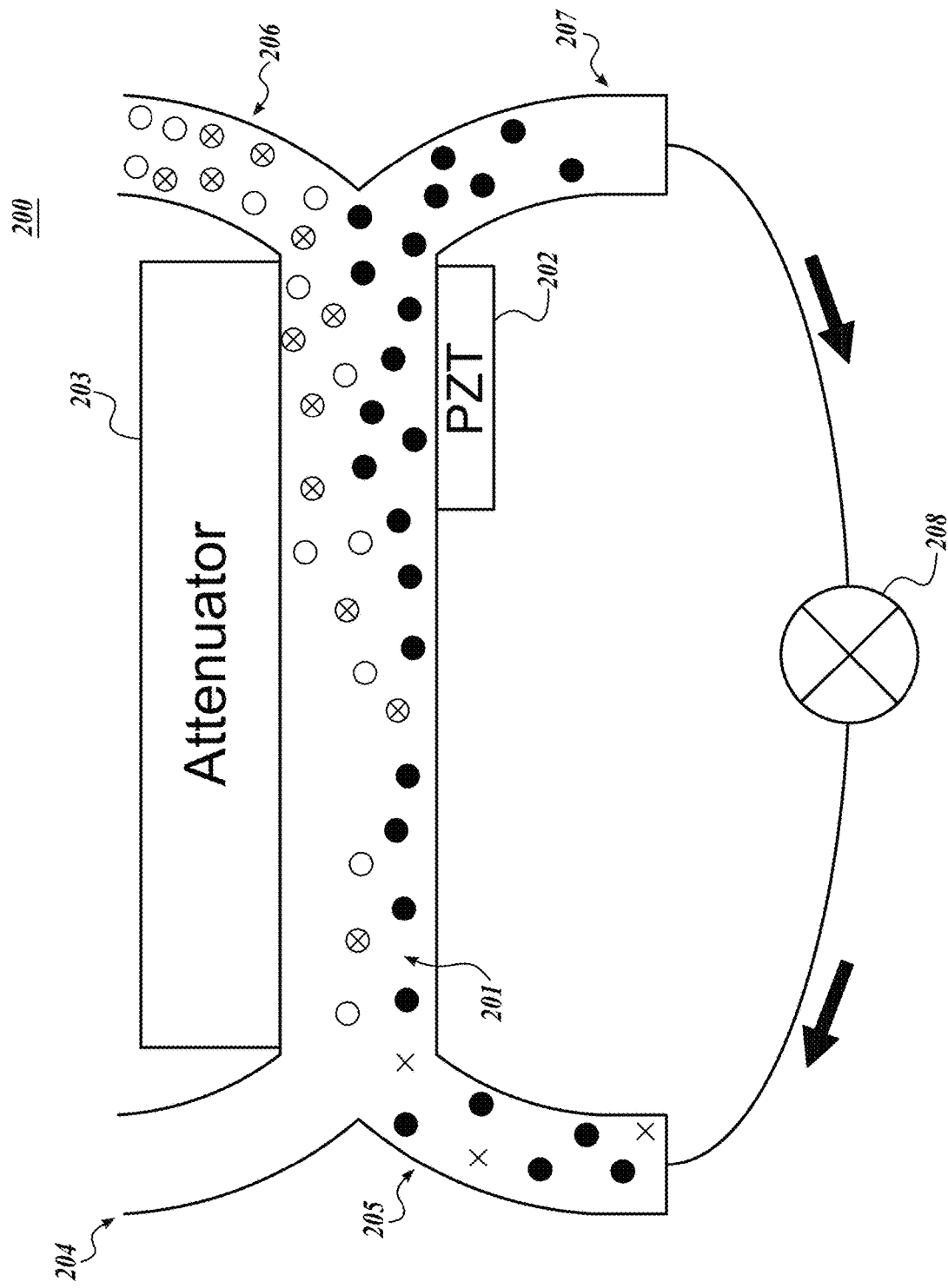
FIG. 3 depicts an exemplary system that can be used to monitor real-time apoptosis in cells treated with an apoptosis-inducing agent. The black circles represent unlabeled cells that are not undergoing apoptosis, the cross marks represent apoptotic unlabeled cells, the white circles represent microbubbles attached to an agent that can bind to an apoptosis marker on cell surface, and the white circles with the cross marks represent apoptotic cells bound to a microbubble.

In some embodiments, the system can be configured to monitor apoptosis in a sample comprising cells, for example, cells that have been treated with a chemotherapeutic agent. An example of such system 200 is illustrated in FIG. 3. System 200 comprises a flow channel 201 and one or more transducers 202 acoustically coupled with the flow channel and an attenuator 203. The system 200 further comprises a recirculating channel 208 connecting the upstream portion and the downstream portion of the flow channel 201. The recirculating channel 208 is configured to return the portion of the flow depleted of microbubble-labeled cells back into the flow cell trough a first inlet channel 205. A sample comprising cells that have been treated with an apoptosis-causing agent, such as a chemotherapeutic agent, is introduced into the system 200 through an inlet channel 205 and mix with sheath flow from an inlet channel 204 into the interaction zone of flow channel 201. Microbubbles labeled with one or more agents that can specifically bind to an apoptosis marker are also introduced into the flow channel and are flowed together with the cells through the flow channel 201. The microbubble agent binds to at least a portion of cells that undergoes apoptosis resulting in microbubble-tagged cells that are then displaced relative to the unlabeled cells upon application of acoustic radiation force and thus can be separated from the unlabeled (i.e., live cells). The ultrasound pulses the labeled cells into a first outlet channel 206, while unlabeled cells (not yet apoptotic) flow into a second outlet channel 207. The portion of the sample comprising cells that are still alive can be returned into the flow channel via recirculating channel 208 and flowed through the flow channel, allowing monitoring of apoptosis in real time.

Thus, in a second aspect, the disclosure provides a method for real-time monitoring of apoptosis in a population of cells suspected to comprise cells undergoing apoptosis, the method comprising:

contacting a sample comprising a population of cells with microbubbles conjugated to an agent that binds to a cell-surface apoptosis marker to form a sample wherein at least a portion of cells undergoing apoptosis is labeled with microbubbles;

flowing the sample wherein at least a portion of cells undergoing apoptosis is labeled with microbubbles through a flow cell comprising an inlet channel, a flow channel having an upstream portion and a downstream portion, an outlet channel, and one or more acoustic transducers acoustically coupled with the flow cell, wherein the one or more acoustic transducers is positioned and configured to deliver a traveling acoustic wave through the flow channel; and applying an acoustic radiation force generated by the traveling acoustic wave to the sample flowing through the flow channel such that the microbubble-labeled cells are displaced relative to unlabeled cells.

In some embodiments of the methods of the disclosure, the flow cell comprises a recirculating channel connecting the upstream portion and the downstream portion of the flow channel and configured to return the portion of the flow depleted of microbubble-labeled cells back into the flow cell.

Any suitable pair of an apoptosis marker and the corresponding agent that binds to the apoptosis marker can be used in the methods disclosed herein, for example, phosphatidylserine and Annexin V.

In some embodiments, the method comprises contacting the sample comprising live cells with an apoptosis-inducing agent prior to contacting the sample with a microbubble conjugate of an agent that binds to a cell-surface apoptosis marker. In other embodiments, the method comprises contacting the sample comprising live cells with an apoptosis-inducing agent simultaneously with contacting the sample with a microbubble conjugate of an agent that binds to a cell-surface apoptosis marker.

In a third aspect, the disclosure provides a method for screening for an apoptotic activity of a therapeutic agent comprising:

contacting a sample comprising a population of cell with a therapeutic agent;

contacting the sample contacted with the therapeutic agent with a microbubble conjugate of an agent that binds to a cell-surface apoptosis marker to form a sample wherein at least a portion of cells is labeled with microbubbles;

flowing the sample wherein at least a portion of cells is labeled with microbubbles through a flow cell comprising an inlet, a flow channel having an upstream portion and a downstream portion, an outlet, and one or more acoustic transducers acoustically coupled with the flow cell, wherein the one or more acoustic transducers is positioned and configured to deliver a traveling acoustic wave through the flow channel; and applying an acoustic radiation force generated by the traveling acoustic wave to the sample flowing through the flow channel such that the microbubble-labeled cells are displaced relative to unlabeled cells.

Apoptosis-inducing agents used herein include experimental chemotherapeutic compounds and approved chemotherapeutics, such as chemotherapeutic agents approved to treat metastatic cancers. In some embodiments, the methods are used to screen experimental apoptotic agents. In other embodiments, the methods are used to select chemotherapeutic agent for a cancer patient. Chemotherapy can useful for treating metastases, but on average only a portion of all tumors respond to the initial choice of drug. Thus patients can suffer from unnecessary side effects of chemotherapy while their tumors continue to grow, until the proper drugs are found. The methods disclosed herein can be used for detection of apoptosis to assess drug efficacy prior to treatment by using tumor cells isolated from a patient to select an appropriate chemotherapeutic agent. In some embodiments, the methods disclosed herein can be used to select the effective dose of a chemotherapeutic agent for a given cancer patient.

As used herein, the term "about" indicates that the subject value can be modified by plus or minus 5% and still fall within the disclosed embodiment.

While illustrative embodiments have been illustrated and described, it will be appreciated that various changes can be made therein without departing from the spirit and scope of the invention. The following examples are provided for the purpose of illustrating, not limiting, the invention.

EXAMPLES

This section is organized as follows. Models for the translational (Sec. IIA) and rotational (Sec. II B) acoustic radiation forces (ARFs) were developed considering the specific conditions of the experiments. A model for the translational ARF was developed for a conjugated cell-MB pair. The rotational ARF was derived for a pair of bubbles conjugated to a single cell which rotates in response to the ARF. This model was developed based on a data set where a cell is adherent to a microscope glass slide. Afterwards, the mode was used to estimate the ARF and resulting velocity of the conjugated pair by comparison with data.

Section III describes the cell and MB preparation (Sec. IIIA), and details of the fixture for taking data under a microscope (Sec. III B). Included in this section is the pressure calibration in a free-field, provided as an upper bound estimate for the pressure amplitude at the cell-MB position.

The results are divided into three subsections. Section IVA describes the observation of the ARF causing a cell to rotate. The cell is conjugated with two MBs, and the theory for the rotational ARF (Sec. II B) was developed specifically for this case. Section IV B describes observations of conjugated cell-MB pairs translating in a stationary (no flow) field. Section IV C describes the ARF under flow with erythrocytes. Only the leukemia cell is deflected, as erythrocytes are not conjugated to MBs expressing anti-CD7 antibodies.

Section V describes some additional features and observations, and some constraints associated with the experiment. For completeness, the ARF for a traveling wave and a standing wave is compared.

II. CALCULATIONS

The problem of interest is the motion of a system of a bubble attached to a cell in response to an ARF at MHz frequencies. The MB (size order 1 μm) is assumed to be in direct contact with the cell (size order 10 μm). Actual separation distances are on the order of nanometers. Section IIA describes translational movement, and Sec. II B describes rotational movement.

A. Translational Movement

The goal was to derive a simple expression that describes how the cell-MB conjugate responds to traveling wave ultrasound pulses.

1. Free Cell

The action of the acoustic radiation force on a free, assumed spherical, cell is considered as follows. A harmonic traveling plane wave acts on a small (relative to the wavelength) spherical particle embedded in a fluid with the radiation force that is directed along the wave propagation direction and has the following expression:

$$F = \frac{4\pi a^2 I}{9 c_0}\left(f_1^2 + f_1 f_2 + \frac{3}{4}f_2^2\right)(ka)^4. \quad (1)$$

Here $a$ is the spherical particle radius, $c_0$ is sound velocity in the fluid, $k=\omega/c_0$ is the acoustic wave number, $\omega$ is the angular frequency, $I=|P|^2/(\rho_0 c_0)$ is the wave intensity, P is the complex acoustic pressure amplitude, $\rho_0$ is the fluid density, and $$f_1 = 1 - \frac{\rho_0 c_0^2}{\rho_p c_p^2}, \quad f_2 = 2\frac{\rho_p - \rho_0}{2\rho_p + \rho_0} \quad (2)$$

are constants which characterize the relative compressibility and density of the sphere material as compared with the surrounding fluid. In Eq. (2), $c_p$ and $\rho_p$ are the sound velocity and density of the particle material.

The velocity u under steady-state motion (for small particles the latter is established quickly) is defined by the balance of the ARF and Stokes friction:

$$u = F/6\pi\eta a \quad (3),$$

where $\eta$ is the fluid viscosity. For estimates, $\rho_p/\rho_0=1:1$ and $c_p=c_0$ were used. Actually, the sound velocities in cancerous cells can differ from that in water, but it would not radically change the result. For $\rho_0=103$ kg/m³, $g=103$ Pa·s (water), and for a particle of radius $a=10$ μm at a frequency of $\omega/(2\pi)=1$ MHz, $u=8.55\times10^{-21}|P|^2$ m/s is obtained, where P is given in Pa. Hence, for P=100 kPa, $u=8.55\times10^{-11}$ m/s=0.0855 nm/s. This motion is most likely not observable.

In a standing wave, the effect can be significantly stronger since the force is proportional to $a^3$ rather than to $a^6$. It can be shown that for the same wave amplitude the ARF from the standing wave is on the order of $(ka)^{-3}$ higher than that of the traveling wave. In the example above this factor is $\sim 10^4$, i.e., the corresponding velocity is on the order of μm/s, which can more readily be detected. Here, however, only consider traveling waves were considered, and thus the ARF acting on the free cell can be considered negligible.

2. Free Microbubble

A free MB insonated with an ultrasonic pulse is described below. Acoustic radiation forces acting on bubbles are called Bjerknes forces. "Primary" Bjerknes forces refer to the interaction between a single bubble and the sound field, and "secondary" Bjerknes forces apply to bubble-bubble interactions when neighbor bubbles attract or repel one another. For bubbles that are small in comparison with the wavelength (i.e., MBs), the primary Bjerknes force F can be represented as:

$$F = -\langle V(t)\nabla p(r,t)\rangle, \quad (4)$$

where V(t) is the bubble volume that oscillates in time t, p(r, t) is acoustic pressure that depends both on time and spatial coordinate r and ⟨ ... ⟩ denotes the time average over the wave period. Equation (4) defines a nonlinear interaction between the monopole pulsation and translational (dipole) oscillations of a bubble. The application described herein involves low pressure amplitudes, and thus linear variations of bubble volume and pressure in Eq. (4). The acoustic pressure in the harmonic wave can be expressed as follows:

$$p = \frac{P}{2}e^{-i\omega t} + \frac{P^*}{2}e^{i\omega t}, \quad (5)$$

where the asterisk denotes the complex conjugate. The radius and volume are perturbations about equilibrium, $R(t)=R_0+\tilde{R}(t)$, where $|\tilde{R}|\ll R_0$, and thus $V(t)=(4/3)\pi R^3 \approx (4/3)\pi R_0^3 + 4\pi R_0^2 \tilde{R}(t)$. In the linear approximation, the bubble radius perturbation in response to the acoustic pressure Eq. (5) also has harmonic behavior:

$$\tilde{R}(t) = \frac{R'}{2}e^{-i\omega t} + \frac{R'^*}{2}e^{i\omega t}, \quad (6)$$

where $R'$ is complex amplitude of $\tilde{R}$. The value of $R'$ can be expressed through the pressure amplitude using the linearized Rayleigh equation. That gives $$R' = \frac{P}{\rho_0 R_0(\omega^2 - \omega_0^2 + 2i\delta\omega)}. \quad (7)$$

Here δ is the total damping constant that accounts for radiation, thermal, and viscous dissipation, and $\omega_0$ is the resonance angular frequency of the bubble. In the case of encapsulated bubbles Eq. (7) can be also used, if the resonance frequency and damping constant are defined from the shell properties. Using the above expressions, the Bjerknes force Eq. (4) then can be expressed as follows:

$$F = \frac{2\pi R_0}{\rho_0}\mathrm{Re}\left[\frac{P^*(r)\nabla P(r)}{\omega_0^2 - \omega^2 + 2i\delta\omega}\right] \quad (8)$$

In the case of a traveling wave, $P(r) \sim e^{ikx}$, where x is distance along the wave propagation direction. Then from Eq. (8) it follows that the vector force F has only a component F along the x-direction, which is expressed as follows:

$$F \approx \frac{2\pi R_0 |P|^2}{\rho_0 c_0 \omega} \frac{1/Q}{(1-\xi^2)^2 + 1/Q^2}. \quad (9)$$

Here $\xi=\omega_0/\omega$ and $Q=\omega/(2\delta)\approx\omega_0/(2\delta)$ is the bubble oscillation quality factor.

In practice it is not important to know what the radiation force is per se, but rather to know the bubble translation caused by that force. Strictly speaking, the full description of the bubble movement should be performed by considering the oscillatory translation of the bubble center due to the instantaneous force $-V\nabla p$ caused by the pressure gradient $\nabla p$. In that description, it is important to account for the fact that the bubble and surrounding fluid move with different velocities. However, at low acoustic pressures, the oscillatory displacement of the bubble center is small. More important is the drift that accumulates over time due to interaction between the monopole and dipole oscillations. This drift of the bubble center can be calculated by averaging the displacement over the wave period. Such an analysis shows that, similar to what has been described for a small spherical particle, the bubble drift velocity u of the steady-state motion is defined by the balance of the ARF and Stokes friction. For simplicity, it is assumed that the Stokes' drag force for encapsulated bubbles can be expressed as for rigid spheres. As a result, the bubble drift velocity is also described by Eq. (3), with the change of the particle radius a by the bubble radius $R_0$. From Eq. (9) the corresponding bubble drift velocity is obtained:

$$u = \frac{|P|^2}{3\eta\rho_0 c_0 \omega} \cdot \frac{1/Q}{(1-\xi^2)^2 + 1/Q^2} \quad (10)$$

It is noteworthy that for weak losses (Q>>1) far from resonance, the bubble velocity is proportional to 1/Q, i.e., in the case of low losses the bubble translation is fairly small in a traveling wave field. However, at resonance ($\xi=1$) the translational velocity is proportional to Q, suggesting that it is more advantageous to operate near the bubble's resonance frequency.

3. Cell-Bubble Conjugate

Now consider the main problem; viz., the motion of the cell-MB coupled system. In this case the driving force is still associated with the bubble, but the viscous drag is due mainly to the much larger cell (it is still considered non-deformable, so that the classic Stokes force should be used). At first glance, the acoustic flow around a bubble attached to a cell is different from that for a free bubble. For instance, if the cell were absolutely rigid, then the resonance frequency of a bubble would decrease: $\omega_{01}=\omega_0\sqrt{\ln 2}$. The cell, however, is not rigid but instead behaves as a 'soft solid', whose Young's modulus is below 10 kPa. Under such conditions, the gelatinous cell influences the bubble oscillation as if it were a fluid. Therefore, it is reasonable to consider the bubble oscillation being identical to that of a free bubble. In particular, if one bubble is attached to a cell, the steady motion of the cell has the following drift velocity (see Eqs. (3) and (9)):

$$u = \frac{R_0}{a} \frac{|P|^2}{3\rho_0 c_0 \omega \eta} \cdot \frac{1/Q}{(1-\xi^2)^2 + 1/Q^2}, \quad (11)$$

which differs from the free bubble expression, Eq. (10), by the ratio of the bubble size to cell size.

Parenthetically, briefly the case where two or more MBs are attached to the cell is considered. If the MBs are separated by a distance much larger than their radii, each MB contributes to the driving force independently and the driving forces can be summed. However, if the separation distance between MBs is comparable with their radii, their interaction can affect such parameters as the bubble resonance frequency, the added mass in the average translational motion, and the mutual MB attraction due to the secondary Bjerknes force (e.g., Refs. 31 and 33). Although such cases were sometimes observed in these experiments, they were not consider here.

Figure 6:
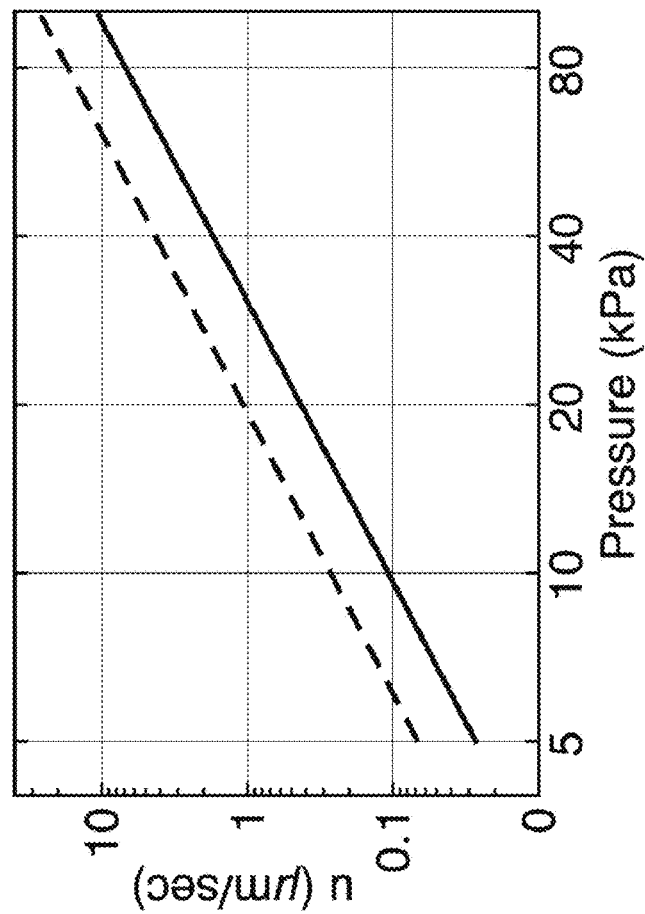
FIG. 6 is a log-log plot of the cell-MB system drift velocity as a function of ultrasonic pressure amplitude. Solid line is for $Q=10$, dashed line is for $Q=4$.

Equation (11) is plotted in FIG. 6 for pressure amplitudes ranging from 5-100 kPa, with the following parameters:

$R_0=1$ μm, $a=5.7$ μm, $\rho_0=1000$ kg/m$^3$, $c_0=1500$ m/s, $\omega/(2\pi)=1$ MHz, $\omega_0/(2\pi)\approx 5$ MHz, $\eta=0.001$ Pa·s, $\xi=5$. Smaller shelled MBs have higher resonance frequencies. A range of estimates for Q was used (S. M. van der Meer, B. Dollet, M. M. Voormolen, C. T. Chin, A. Bouakaz, N. de Jong, M. Versluis, and D. Lohse, "Microbubble spectroscopy of ultrasound contrast agents," *J Acoust Soc Am* 121, 648-656 (2007)). For an $R_0=1.9$ μm, $Q\approx 4$, while for an $R_0=1.2$ μm, $Q\approx 10$. Both values are plotted, providing a range of drift velocities for a given pressure amplitude.

B. Cell Rotation

Figure 7:
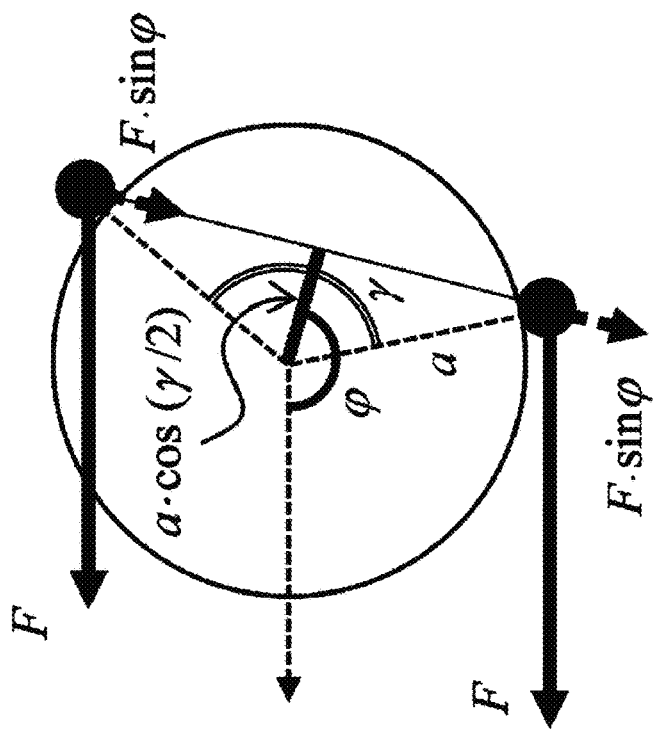
FIG. 7 shows two bubbles sitting against a spherical cell of radius a. An arm (black line) bisects the midpoint of the line connecting the bubbles. The arm length is $a \cdot \cos(\gamma/2)$, where angle $\gamma$ is the angle between the lines that connect the center of each bubble with the center of the cell. Both bubbles experience the same radiation force F shown by solid arrow. The corresponding torque acting the cell from each bubble is expressed as a product of the force projection $F \cdot \sin \varphi$ and the arm length, which results in the net torque $T = -2 \cdot F a \cdot \sin \varphi \cos(c/2)$.

The following model was developed to describe an experimental observation, the rotation of a cell with two conjugated MBs. Let us assume that (1) there are two identical bubbles and that they occupy the central cross-sectional plane, (2) the radiation forces acting on the bubbles are equal, and (3) those forces are parallel to that plane, as illustrated in FIG. 7. As for the force direction, let us assume that the final position of the cell-MB conjugate corresponds to the equilibrium when the line that connects the two bubbles is perpendicular to the force direction. A bubble's acceleration or deceleration causes movement of some volume of the surrounding fluid. The correspondent fluid mass (added mass) is equal to half the volume of the sphere times the density of the fluid. The bubbles are much smaller than the cell, so as with the previous case, that added mass can be considered to be negligible.

Let us consider the midplane geometry shown in FIG. 7, where two MBs are adherent to a spherical cell of radius a. An arm (black line) bisects the midpoint of the line connecting the bubbles. The corresponding angle is marked by $\varphi$. The length of the arm is a $\cos(\gamma/2)$, where $\gamma$ is angle between the radius-vectors of the bubbles. Both bubbles experience the same radiation force F shown by red arrow. The projection of these forces perpendicular to the arm is $F \cdot \sin\varphi$. The net torque is thus $\tau=-2aF\cos(\gamma/2)\sin\varphi$.

A sphere of radius a rotating with angular velocity $\Omega=d\varphi/dt$ is influenced by the viscous torque $$T_{vis}=-8\pi\eta a^3 \Omega \quad (12)$$

The mass moment of inertia of a solid sphere of radius a and mass M is given by:

$$I=\tfrac{2}{5}Ma^2=\tfrac{8}{15}\pi\rho_{cell}a^5 \quad (13)$$

The equation of motion is:

$$I\frac{d^2\varphi}{dt^2}=T+T_{vis} \quad (14)$$

This gives:

$$I\frac{d^2\varphi}{dt^2}=-2Fa\cos(\gamma/2)\cdot\sin\varphi - 8\pi\eta a^3 \frac{d\varphi}{dt}, \quad (15)$$

which describes a classical pendulum. It is convenient to rewrite Eq. (15) in the following form:

$$\frac{d^2\varphi}{dt^2}+2\delta\frac{d\varphi}{dt}+\omega_*^2\sin\varphi=0, \quad (16)$$

where $$\delta=\frac{4\pi\eta a^3}{I}=\frac{15\eta}{2\rho_{cell}a^2} \quad (17)$$

$$\omega_*=\sqrt{\frac{2Fa\cos(\gamma/2)}{I}}=\sqrt{\frac{15F\cos(\gamma/2)}{4\pi\rho_{cell}a^4}}$$

Later, by comparing solutions of Eqs. (16-17) with data, the ARF, F is extracted. Also, it is worth noting that if the angle, $\varphi$, changes slowly, it is reasonable to neglect the first term in the left-hand-side of Eq. (16), so that $$2\delta\frac{d\varphi}{dt}+\omega_*^2\sin\varphi\approx 0. \quad (18)$$

This 1st-order differential equation can be easily integrated:

$$\cos\varphi=\tanh\left(\frac{\omega_*^2}{2\delta}t+\text{arctanh}(\cos\varphi_0)\right), \quad (19)$$

or, in terms of the rotation angle, $$\varphi=\arccos\left[\tanh\left(\frac{\omega_*^2}{2\delta}t+\text{arctanh}(\cos\varphi_0)\right)\right] \quad (20)$$

The solutions, Eqs. (16), (19), and (20) are compared with the experimental data in Sec. IVA.

III. EXPERIMENTAL DESIGN

A. Cell And Microbubble Preparation

Leukemia cells were selected for these proof-of-principle studies because of the well-known antigens expressed on them; for example, CCL 119 cells have the following antigens with variable frequencies of occurrence on individual cells within a population: CD3 B (37%), CD 4 (50%), CD5 (95%), and CD7 (77%), where the percentages express the frequency of occurrence of that particular antigen. The cell must express a surface marker, it cannot be an intracellular marker, as the MBs are too large to penetrate the cell membrane. TargeStar-SA MBs (Targeson, San Diego, Calif.) were used for these studies. The MBs are lipid-shelled and labelled by the manufacturer with streptavidin. Typical MB concentrations are 1.9-2.5×10$^9$ MB s/mL, with an average diameter of about 2 μm and an average streptavidin loading of 1×10$^5$ molecules/MB. The manufacturer's preparation instructions called for labelling the contents of an entire vial of MBs with the biotinylated antibody of choice. Because this approach would use unnecessarily large amounts of antibody, a different approach was used by first washing, concentrating and incubating the cells with biotinylated anti-CD7, washing them again, and then incubating the antibody-labelled cells with the streptavidin-labelled MBs. Very conservative quantities of antibody were used, and cell-MB conjugation rates were very high (294 of 295 observed cells were conjugated with at least 1 MB). CCL-119 human leukemia cells were obtained from the American Type Culture Collection (ATCC, Manassas, Va.). They were cultured in suspension at 37° C. under a 5% CO$_2$ atmosphere in a high glucose formulation of RPMI 1640 medium containing L-glutamine and HEPES, supplemented with 10% fetal bovine serum and 1% penicillin-streptomycin solution (ATCC, Manassas, Va.). For experimental use, cell concentrations were measured using a Z1 Coulter Counter (Beckman-Coulter, Brea, Calif.). Five to six million cells were concentrated by centrifugation (300 g-5 min, 3° C.) in 15 mL centrifuge tubes. The pellets were re-suspended in 500 lL of Dulbecco's phosphate buffered saline containing 10% FBS, and the cells transferred to microcentrifuge tubes. Four 250 µL rinses of the 15 mL tube followed, pooling the recovered rinsate with the contents of the microcentrifuge tube, and the resultant 1.5 mL of cell suspension was recentrifuged to wash the cells. This wash step was repeated once. The last supernatant was then drawn off as completely as possible without loss of the pelleted cells (50 µL remaining), and an aliquot delivering between 0.5-1.0 µg of biotinylated mouse monoclonal anti-CD7 antibody (Abeam, Cambridge, Mass.) per million cells was added, bringing the total volume to 100-150 µL. The cell and antibody mixture was allowed to react for 30-45 min at 3° C. The cells were then washed twice as described above to remove any unbound antibody and this reduce potential competition between unboundand MB-bound anti-CD7 for CD7 binding sites on the cell surface. Following labeling the cells with anti-CD7, the concentrated cells were then reacted with TargeStar SA MBs using a 1:1 volume ratio. This preparation went directly (i.e., without further washing) to the microscopy and micro cinematography lab, where they were diluted with PBS as necessary to produce optical fields containing many cells but not so many as to obscure the view of individual cells.

B. Apparatus

Figure 8:
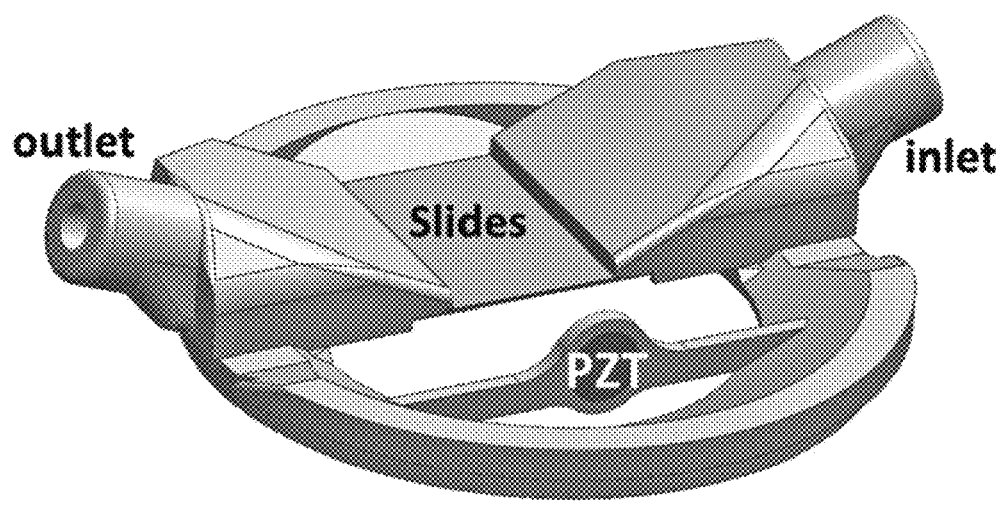
FIG. 8 shows the experimental apparatus, in accordance with the present disclosure, used to generate cell images. Microscope coverslips were sandwiched together, separated by 87-lm wires attached at the corners. The slips were mounted to a 3-D printed fixture so that a suspension of cells could flow between them. A PZT transducer operating at 1 MHz generated pulses of ultrasound that displaced cell-MB conjugates. The entire housing was submerged in degassed water and aligned under a microscope for imaging.

The experimental apparatus used to study exemplary cell separation is illustrated in FIG. 8. It was designed to use with an inverted microscope to image the cell-MB pairs. The viewing chamber was made from two microscope slide coverslips that were brought together to form a small rectangular volume. A strand of 87 µm diameter wire was placed at each corner with a small amount of epoxy to bond the coverslips together while creating a small gap between them. In addition, a small amount of epoxy was placed along the length of the coverslips (proximal and distal to the transducer) under a microscope to create a seal. This allowed fluid (viz., cell suspensions) to flow from the input port, through the gap between the coverslips, and to drain through the output port. The bonded viewing chamber was then affixed to a three-dimensional (3-D) printed housing. In particular, the round ports reshaped into flat slits to more readily allow the suspensions to flow through the flat view chamber. A 9 mm diameter PZT was press-fitted into a slot orthogonal to the flow direction, centered in the same plane as the coverslips. The total exposed area of the slides was approximately 2×2 cm (the imaging field of view under a 10× objective was less than 12×1 mm). The PZT was driven by a function generator (model HP 33120A). Notably, there was no amplification, no matching network, nor a matching layer applied to the transducer. At different times, the transducer was driven by a voltage from 1 to 10V (pk-pk). Specific voltages used are listed below.

Figure 9:
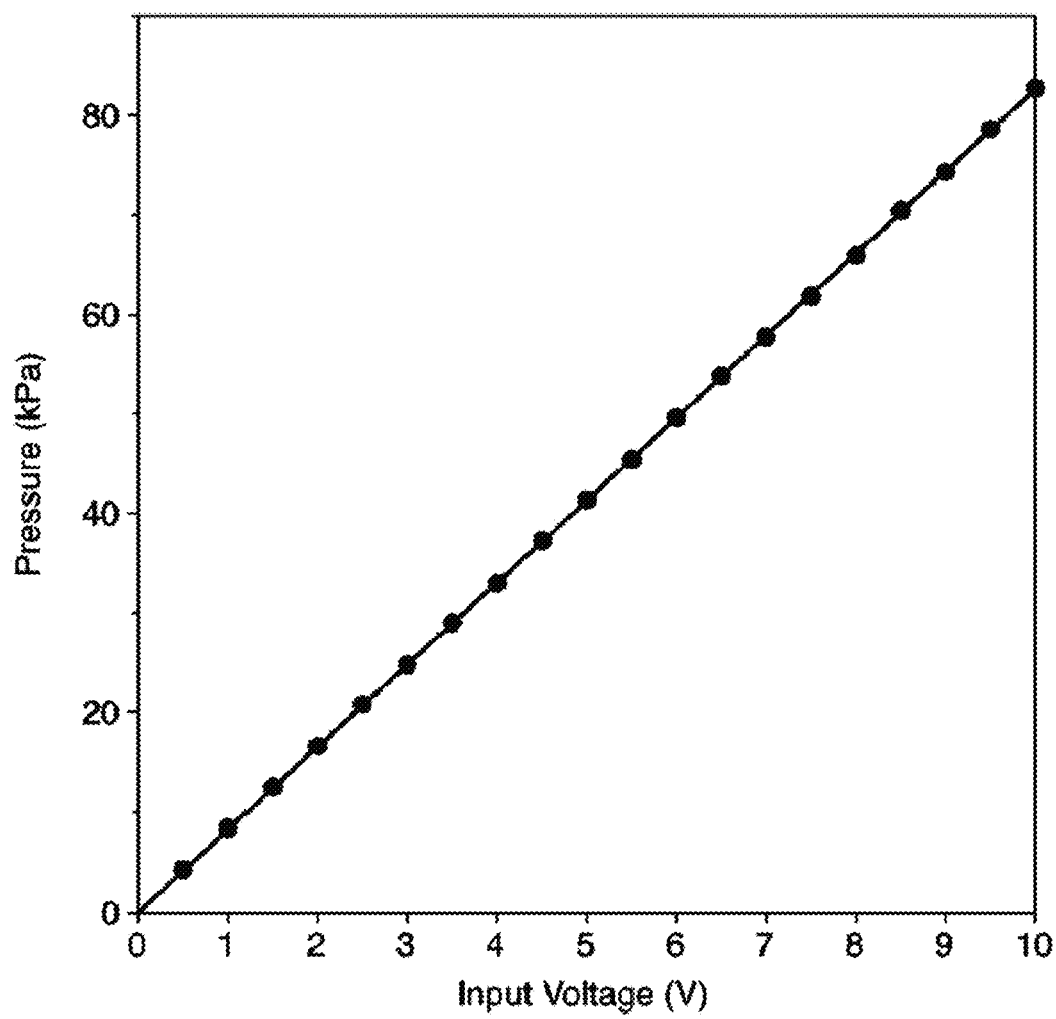
FIG. 9 is a calibration curve of the PZT transducer output. An Onda hydrophone, model HGL-0200 was used to measure the pressure amplitude at the focus in free field as a function of input voltage (pk-pk).

The pressure amplitudes inside the 80 µm gap between the coverslips could not be measured. Instead, after the study, the inlet and outlet ports, as well as the coverslips, were removed. The PZT, still in the fixture, was placed in a degassed water tank for pressure measurements at various driving voltages. A calibrated Onda HGL-0200 hydrophone was used with an AH-2020 preamp (Onda Corp., Sunnyvale, Calif.). The hydrophone was mounted on a three-axis translation stage, while the transducer apparatus was fixed in place. The hydrophone was scanned until the maximum pressure was measured. Pressure amplitudes were then recorded for voltages ranging from 0.5 to 10V (pk-pk). The results are shown in FIG. 9, along with a linear best-fit curve. Although it was impossible to measure the acoustic field between the coverslips, COMSOL was used to estimate the uniformity of the pressure field. The results (not shown here) suggest that the pressure field was relatively uniform within the microscope's field of view of approximately 1×1 mm.

IV. RESULTS

A. Initial Response—Cell Rotation

Figure 10A:
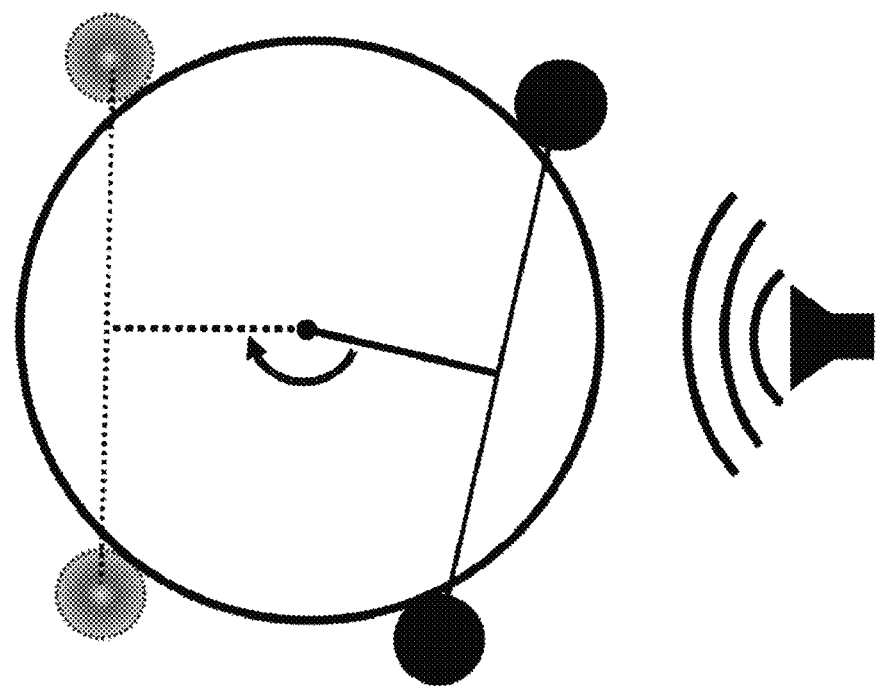
FIG. 10A illustrates cell rotation. The cell-MB conjugate rotates until the pair is aligned to the ultrasound field. Quantification of cell rotation is shown in FIG. 10B. The solid line is the solution to Eq. (11). The final angle is arbitrarily labeled as 0 degrees.
Figure 10B:
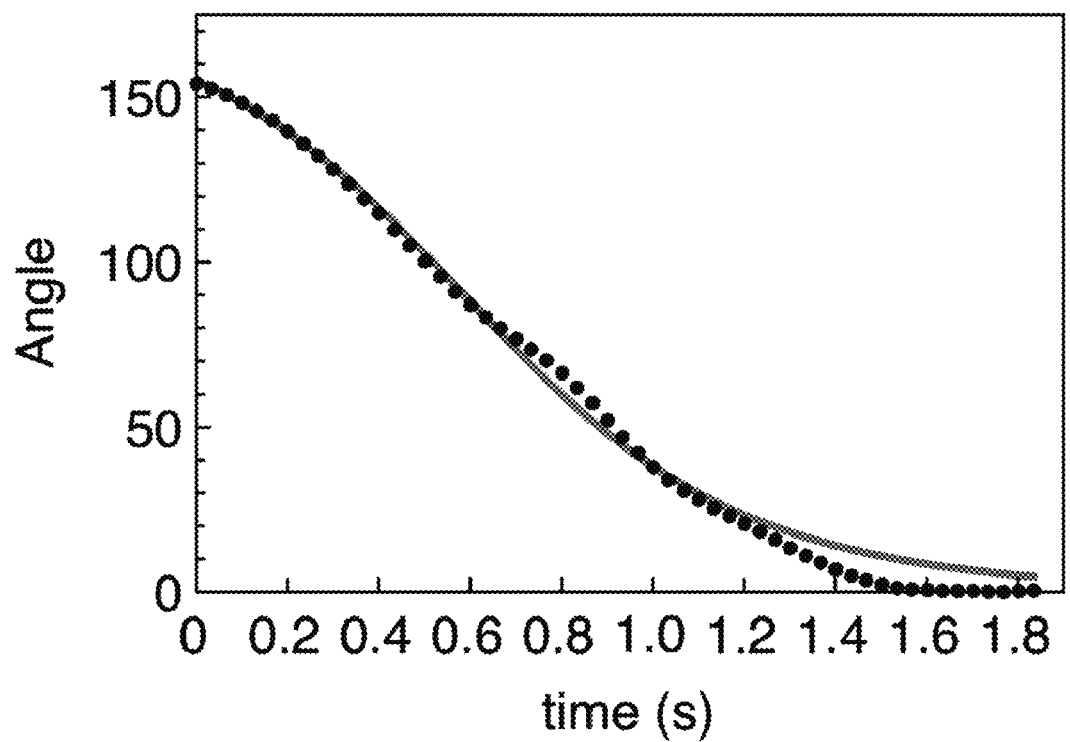

As described in Sec. II, a MB is much more susceptible to an ultrasound pulse than is a cell, whereas a cell conjugated with a MB acts predominantly to induce a drag on the MB's motion. Because of this, when the coupled cell-MB pair is initially insonated, the pair will orient itself to the direction of the ultrasound pulse. That is, the cell will rotate until the cell-MB conjugate is aligned with the ultrasound beam. A particularly impressive display of this was captured on video and quantified below. A leukemia cell was observed with two MBs attached. Under CW insonation with 2 Vpk-pk (ultrasound direction given by arrow), the cell rotated around its center of mass. From this observation, it was possible to calculate the rotation angle as a function of time, shown in FIGS. 10A and 10B (the angle is relative, the final position was labeled as 0°). After about 1.5 s, the cell-MB conjugate aligned with the ultrasound field, and no further rotation was observed.

From Eq. (19) it follows that the radiation force can be extracted from the observations by considering the following linear dependence:

$$\text{arctanh}(\cos \varphi) = \text{arctanh}(\cos \varphi_0) + \frac{\omega_0^2}{2\delta} t = const + F \cdot \frac{\cos(\gamma/2)}{4\pi\eta a^2} \cdot t. \quad (21)$$

Figure 11:
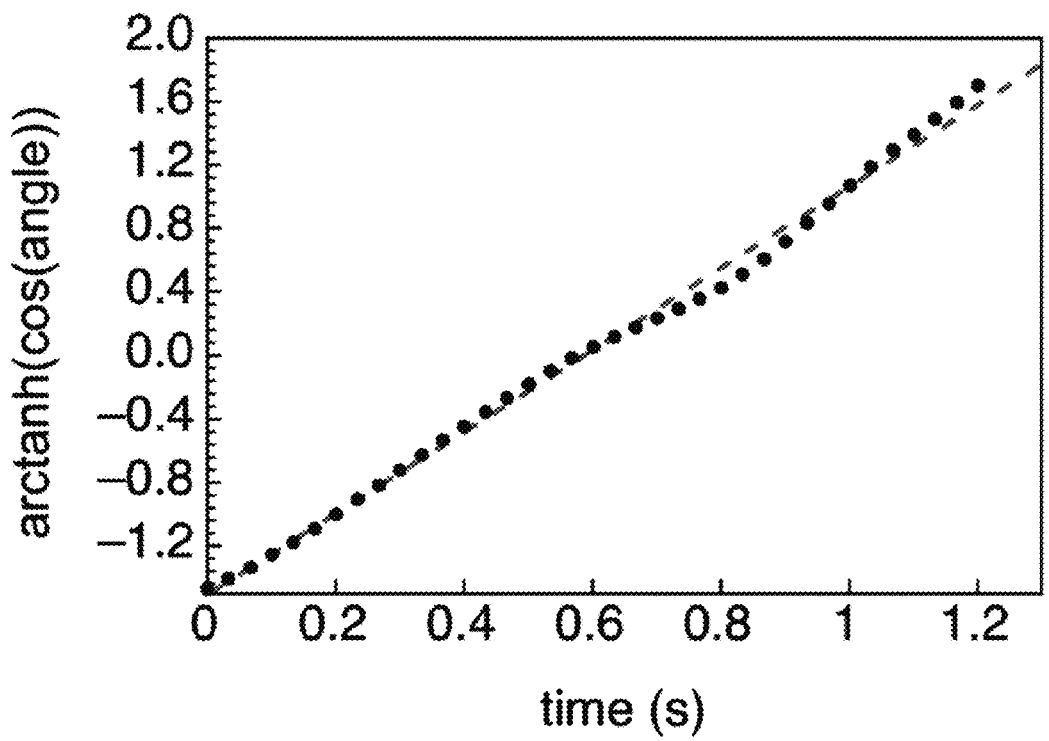
FIG. 11 shows the data from FIG. 10B re-plotted using the linear Eq. (12). The best fit line to this equation is $y=2.572 x-1.51$, with an $R^2=0.9956$. Comparing to Eq. (12), the force can be extracted, in this case, $F=1.7\times10^{-12}$ N.

Equation 12 is compared with the data by plotting the arctan h(cos(φ)) as a function of time (FIG. 11), along with a best fit straight line. There is a very good correlation ($R^2=0.9956$). The straight line corresponds to F cos(γ/2)/ $(4\pi\eta a^2) \approx 2.57$, which gives F≈1.7·10$^{-12}$ N. Here the following parameters were used: γ=104°, η=0.001 Pa·s, and a=5.7 µm. The cell radius a was taken as half of the average cell diameter calculated from individual measurements of 163 living CCL119 cells (11.37±1.94 µm). It's worth comparing the ARF extracted from the data with a calculation of the ARF from Eq. (9). The contribution of the cell can be ignored because the ARF is dominated by the MB. Using $R_0=1$ µm, P=80 kPa, and Q=4, the ARF acting on the cell-MB conjugate was found to be F=1.85 10$^{-12}$ N. The model compares reasonably well with the data-extracted value, especially given the uncertainties in the model variables.

Finally, let us estimate the cell velocity when it is moving under the radiation force that acts only on the MBs but not on the cell. According to Stokes' law, 2F=6πηav, from where v=F/3πηa. For F N it was obtained: v=31.6 µm/sec.

B. Translation without Flow

If the cell is not fixed in space, not only will it rotate, but in a traveling wave it will also translate in the direction of the ultrasound pulse. Observations show the cell rotates to align with the sound field. The stable equilibrium position is such that the MB is dragging the cell behind it.

Figure 12A:
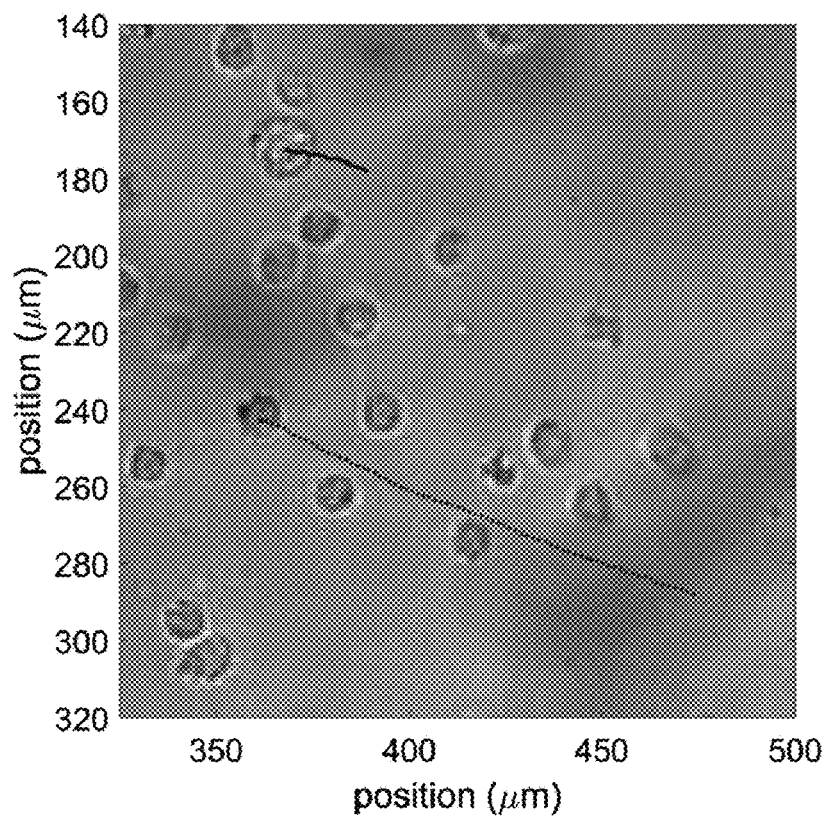
FIG. 12A shows analysis of cell-MB pair movement in response to an ultrasound pulse.

The translational velocity of the pair depends not only on the pressure amplitude, but also on the number of attached MBs. This is illustrated in FIGS. 12a and 12B, where an analyzed image is shown with two cell-MB pairs being pushed through a field of other cells. From the video, one can observe two cells being pulled by attached MBs under the ARF. The upper cell's motion is highlighted in blue, while the lower cell is highlighted in red. Noticeably, the lower cell moves about 5× faster than the upper cell. The difference in velocity is partly due to the size difference in cells, and also to the number of MBs attached to the cells. The upper cell has one attached MB. The lower cell appears to have three attached MBs, as shown in FIGS. 13A and 13B. Assuming the MBs are acting independently, the lower cell would be expected to move 3× faster than the top cell. But the velocity is also proportional to (1/size), and the bottom cell is about ⅗ the size of the upper cell. Therefore, the relative difference in the velocities is 3×(5/3×)=5×, which agrees with the video analysis.

For these preliminary studies, the average drift velocity of 7 cell-MB conjugates at either 40 or 80-kPa, was quantified and shown in Table I. The listed pressure is the maximum free-field amplitude. The actual amplitudes at the location of the conjugates are unknown (i.e., doubling the pressure amplitude should increase the velocity by 4×). Other factors that may influence the results are discussed in Sec. V.

TABLE I

Averaged drift velocities of cell-MB conjugates.

| Pressure (kPa) | | | | | | |
|---|---|---|---|---|---|---|
| 40$^a$ | 40$^a$ | 40$^a$ | 80$^a$ | 80$^a$ | 80$^a$ | 80$^a$ |

| Drift velocity (μm/s) | | | | | | |
|---|---|---|---|---|---|---|
| 2.3 | 0.5 | 2 | 12 | 18 | 26 | 20 |

$^a$Maximum pressure measured in the free field, not between the coverslips.

C. Translation Under Flow

In cell sorting applications, the goal is to isolate different cell types according to the presence or absence of unique cell surface characteristics. In FACS systems and some MACS systems, this is accomplished under flow. Indeed, the goal of this disclosure is to develop the technology so that tagged cells are forced out of the main flow for isolation or sorting. To determine the feasibility of separating tagged cells from untagged ones, leukemia and anticoagulated erythrocytes were mixed in a vial and injected the cell suspension into the view chamber apparatus (FIG. 8).

During operation, a syringe pump would flush the system with saline prior to adding the cells. Once the saline started to flow from the output port, the saline-filled syringe would be replaced by a syringe containing the mixed cell suspension, and the operator would view a region of interest (ROI) until cells began to flow by. The operator would then begin collecting video data and manually activate ultrasound pulses. After a few minutes, the ROI would often become congested with cells sticking to the glass coverslips, so the ROI would be moved until a new area with sparse adherent cells was found. This was repeated over approximately 10 min. Several of these studies were performed over several days. Movies were downloaded for later processing. Most movies showed incomplete events; in some cases, the action of the ultrasound pulse occurred when the coupled cell-MB conjugates were out of focus, making it difficult to clearly observe how they responded. In other cases, the conjugates were too close to the upper coverslip and their ultrasound-induced translation was impeded or arrested when they interacted with the coverslip. In still other cases, the translating conjugates collided with other, untagged cells that were blocking the path.

Figure 14:
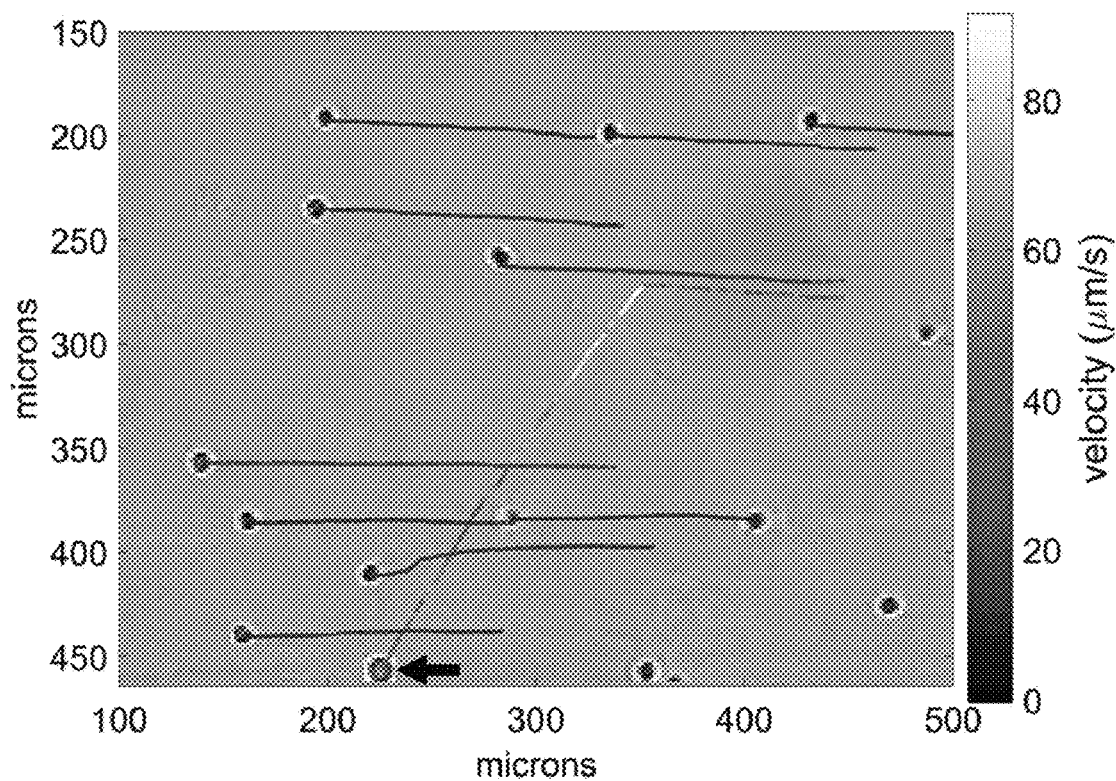
FIG. 14 shows the paths of individual cells (erythrocytes and leukemia cell (marked with arrow)) under flow, obtained from a video recording cell movement. The cell locations shown correspond to the end of the highlighted path. The erythrocytes flow horizontally right to left and are barely disturbed when the ultrasound is turned on. The leukemia cell, on the other hand, changes direction and displaces in the direction of the ultrasound pulse. The calibrated images show the actual velocities. The erythrocytes flow at a velocity of about 20 μm/s. The leukemia cell initially flows at about 40 μm/s. When the ultrasound is turned on, its velocity increases to about 90 μm/s before slowing down to about 50 μm/s. For analysis, cells were manually selected in the first frame in the video series and tracked using translational cross-correlation over the remaining frames in the series. The resulting correlation was fit to a paraboloid to compute sub-pixel resolution displacements.
Figure 15:
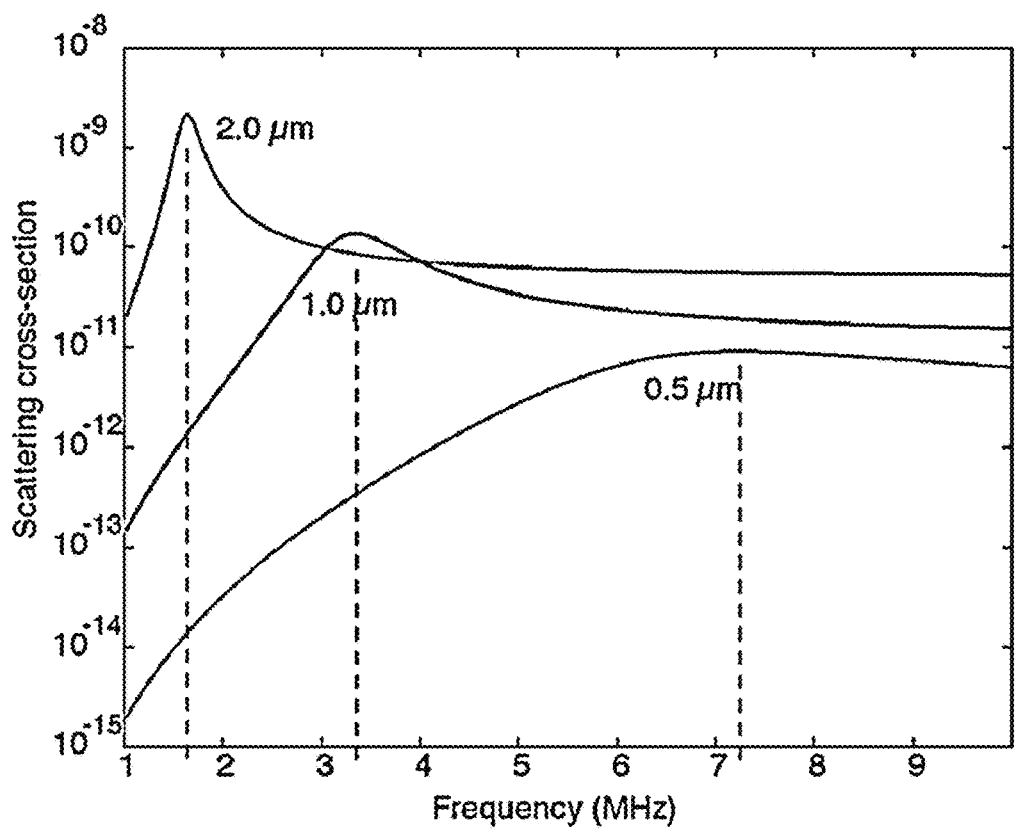
FIG. 15 demonstrates that resonance frequency depends on bubble size. Bubble interaction with sound field is maximum at the resonance frequency.

The data shown in FIG. 14 illustrate one example where video evidence was not compromised. In this data, a relatively sparse number of erythrocytes are seen traversing the field of view in response to flow. Then, a leukemia cell enters from the right. It is traveling faster than the erythrocytes. When the cell nearly reaches the midpoint of the field of view, the ultrasound is turned on, and the cell is displaced relative to the erythrocytes. In the video, the change in direction of the cell is immediate and significant. The dimensions and velocities were obtained by calibrating the microscope against a 10-μm calibration slide. Video analysis was used to track the motion of the cells. Cells were manually selected in the first frame in the video series and tracked using translational cross-correlation over the remaining frames in the series. Some, but not all of the erythrocytes were tracked to show their paths before and after the ultrasound was turned on. The cell locations shown correspond to the end of the highlighted path.

D. High-Throughput Sorting

The application of this technology may be useful for large scale (positive or negative) sorting, as well as rare cell sorting. A simple test was performed with a much more concentrated suspension of leukemia cells and erythrocytes. In this case, the concentration was approximately 100× higher than that shown in FIG. 14. A filtering approach based on velocity was implemented to visually differentiate tagged and untagged cells; tagged cells moved significantly faster than untagged cells when ultrasound was applied. High velocity tagged cells were filtered out of the video sequence using a low-pass Butterworth filter applied to each pixel across all video frames. The average residual powers for each pixel were then assigned to the blue channel of an RGB image. Low velocity cells were similarly filtered out using a high-pass Butterworth filter with the residual power assigned to the image's red channel. The displacement of tagged leukemia cells was clearly seen. In some cases, the paths were not straight lines. Without wishing to be bound by theory, it was presumed that the cells collided with untagged cells, causing distortion of the path. In addition, the secondary Bjerknes force will cause an attraction between two MBs of nearly the same size.

V. DISCUSSION

The present disclosure demonstrates the feasibility of pushing conjugated cell-MB pairs via ultrasound pulses in a flow system under propagating (not standing) waves. For a model system, leukemia cells were chosen and targeted with the MBs bound to anti CD7 antibodies. The examples showed displacement of the conjugated pairs relative to non-conjugated (erythrocyte and/or leukemia) cells in a model system under both stationary and flow conditions. The simplified model for the velocity of the coupled pair from Eq. (11) is not expected to agree quantitatively with the data, as there are several unknown parameters. However, the calculated drift velocity obtained from the rotation data had good agreement with the experimental observations.

A. Standing Vs Traveling Waves

It is worth examining the differences between a system employing a traveling wave mode, and one with standing waves. As discussed in Sec. IIA, the Bjerknes force for a traveling wave follows from Eq. (8) using $P=Ae^{ikx}$:

$$F_{traveling} = \frac{4\pi R_0 A^2 \omega^2}{\rho_0 c_0} \frac{\delta}{(\omega^2 - \omega_0^2)^2 + (2\delta\omega)^2} \qquad (22)$$

Here $A=|P|$ is the real amplitude of the traveling wave $P=Ae^{ikx}$. For a standing wave, the complex acoustic pressure amplitude changes to $P=A\cos(kx)$, and Eq. (8) results in the corresponding radiation force:

$$F_{standing} = \frac{\pi R_0 P^2 \omega}{\rho_0 c_0} \frac{(\omega^2 - \omega_0^2)}{(\omega^2 - \omega_0^2)^2 + (2\delta\omega)^2} \sin(2kx) \qquad (23)$$

According to Eq. (22) and its approximate version, Eq. (9), a traveling wave always pushes the bubble along the propagation direction; i.e., away from the source. For a standing wave, Eq. (23) shows that the force is equal to zero at pressure nodes and antinodes, and the force is directed toward a pressure antinode for small bubbles (smaller than the resonance size: $\omega<\omega_0$), and the force is toward a pressure node for large bubbles (larger than the resonance size: $\omega>\omega_0$). It is interesting to compare the absolute values of these forces. Let's use the bubble oscillation quality factor $Q=\omega_0/(2\delta)$, the wave frequency normalized by the bubble resonance frequency $\overline{\omega}=\omega/\omega_0$, and a characteristic value for the force:

$$F_0 = \frac{\pi R_0 P^2}{\rho_0 c_0 \omega_0}. \qquad (24)$$

Then the expressions for the forces become dimensionless and thus easier to compare:

$$\frac{F_{traveling}}{F_0} = \frac{2\overline{\omega}^2/Q}{(\overline{\omega}^2 - 1)^2 + (\overline{\omega}/Q)^2} \qquad (25)$$

$$\frac{F_{standing}}{F_0} = \frac{\overline{\omega}(\overline{\omega}^2 - 1)}{(\overline{\omega}^2 - 1)^2 + (\overline{\omega}/Q)^2} \qquad (26)$$

Figure 18:
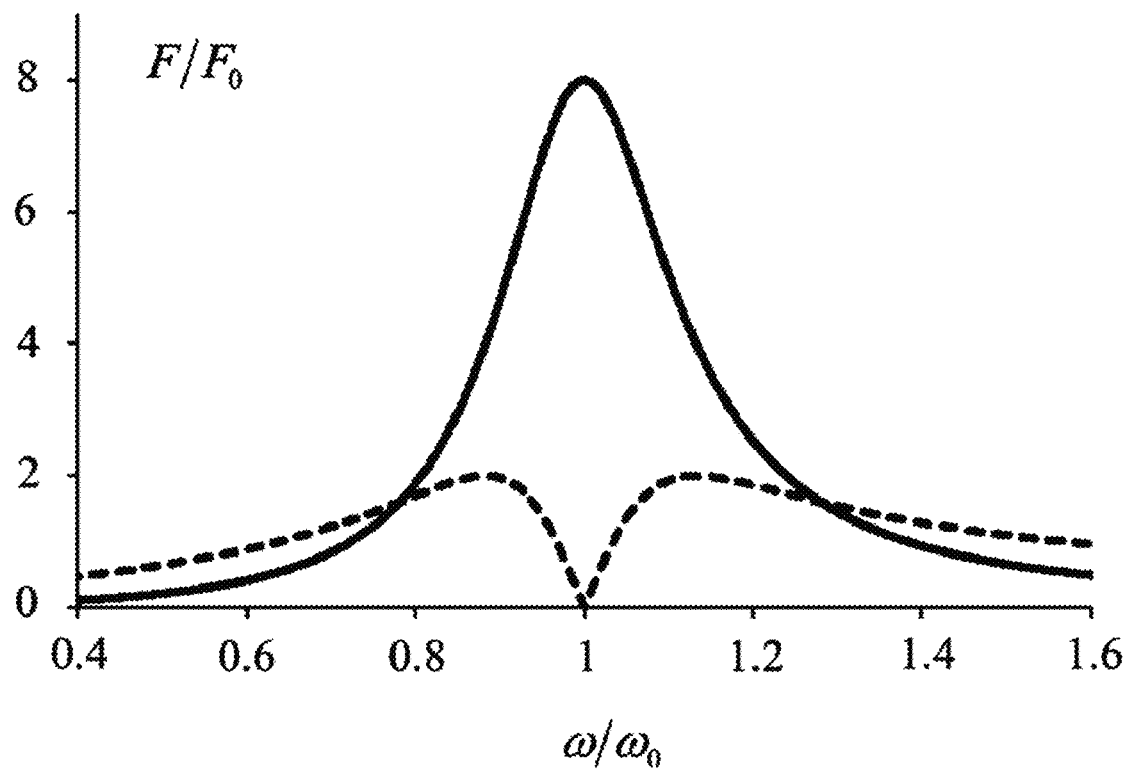
FIG. 18 is a plot of magnitude of the normalized radiation force/$F_0$ on a bubble with Q=4 versus normalized frequency $\omega/\omega_0$ in a standing or traveling wave: $F_{traveling}/F_0$ is shown with a solid line and $F_{standing}/F_0$ is shown with a dashed line. The standing wave has a null exactly at resonance, but far from resonance, the force is larger than for traveling waves.

Typically, a gas bubble quality factor is around $Q\approx 10$. Using that assumption, the frequency dependence of forces is plotted in FIG. 18. From these curves the following conclusions can be made: (1) In both cases the most efficient forcing happens when the frequency is close to the resonance frequency. In the best case, the propagating wave creates a radiation force four times higher than does the standing wave. (2) For a propagating wave, it is best to be near resonance. (3) If one chooses the near-resonance case for the standing wave, it is more efficient to be a little bit off resonance: the best case is when $f/f_0=0.95$ or $1.05$. Here $f=\omega/(2\pi)$ is the driving frequency, and $f_0$ is the bubble resonance frequency. When the drive frequency is exactly at resonance, the force is equal to zero. (4) When the bubble is driven far from the resonance, the standing wave becomes more efficient.

These results suggest that the most efficient paradigm for acoustic forcing of cell-MB conjugates is a traveling wave system using MBs with a very narrow size distribution and driven near their resonance frequency. An added advantage of traveling waves is the ability to displace the cell-MB conjugates over larger distances than a half-wavelength. Also, standing waves require a tighter control of tuning.

B. Faster Vs Slower Movement

One would expect that, in the absence of other forces, all particles should flow with the fluid at approximately the same velocity. However, the initial velocity (prior to initiating the acoustic pulse) of tagged leukemia cells was noticeably higher than the erythrocytes. Variations in fluid velocity within the <1 mm field of view is probably precluded, given the slow (and presumably laminar) flow. A probable explanation is that the particles are not located at the same plane. In the experimental system, it was assumed that the cross-sectional flow was parabolic, and the coverslips presented no-slip boundary conditions. The microscope was focused near the upper coverslip. The leukemia cells may be slightly below the erythrocytes, putting them in a faster flow stream. Further, the system's depth of field was relatively narrow. Further, the system's depth of field was relatively narrow. The depth of field is given by $$d = \frac{\lambda\sqrt{n^2 - NA^2}}{NA^2} \qquad (27)$$

where d is the depth of field, n is the index of refraction (in this case, air=1), and NA is the numerical aperture. A Nikon CFI Plan Fluor 10× objective was used which has an NA=0.3. For an average optical wavelength of $\lambda=500$ nm, $d=5.3$ μm. This is about the diameter of an erythrocyte (6-8 μm), and less than half the diameter of a leukemia cell. The leukemia cells are slightly less focused than erythrocyte, suggesting they were in a slightly different (lower) plane, and thus subject to a slightly different (higher) flow velocity.

C. Conjugate Velocities

Table I lists the drift velocity from several observations. Although quantitative, there are several issues which limit the interpretation of these values. First, the actual pressure amplitude at the location of the cell-MB conjugate is unknown. Only the maximum free-field amplitude is known. The conjugates most likely experienced a different pressure amplitude. Second, in some cases the conjugates may have experienced additional drag from sticking, or being close to, the coverslip surface. Finally, the actual number of MBs conjugated to the cell is unknown. There may have been other attached MBs that were out of the image plane, and thus not seen. The drift velocity would be affected by these additional MBs, as described in Sec. IV B. Among future refinements will be to better control the number of MBs conjugated to cells, allowing for more accurate comparative studies.

VI. CONCLUSION

The isolation and sorting of cells is an important process in research and hospital labs for purifying cell lines. Although FACS and MACS are available, they can be unwieldy to use, expensive, or time consuming. The disclosure demonstrates feasibility of using ultrasound and tagged MBs as a means to isolate, enrich, sort and purify cells with specific cell surface antigens as a first step in developing a high-throughput, easy-to-use and inexpensive MiCS cell sorter.

The invention claimed is:
1. A cell-sorting system comprising:
 a flow cell for flowing a sample comprising microbubble-labeled cells and unlabeled cells, wherein the flow cell comprises one or more inlet channels, a flow channel having an upstream portion, upstream of one or more acoustic transducers relative to a direction of sample flow through the flow channel, and a downstream portion, downstream of the one or more acoustic transducers relative to a direction of sample flow through the flow channel, and one or more outlet channels; and the one or more acoustic transducers acoustically coupled with the flow cell, wherein the one or more acoustic transducers is positioned and configured to deliver a traveling acoustic wave through the flow channel to apply an acoustic radiation force to a sample flowing through the flow channel such that the microbubble-labeled cells are displaced relative to unlabeled cells along a direction of the acoustic radiation force away from the one or more acoustic transducers, the direction of the acoustic radiation force being transverse to the direction of sample flow.

2. The cell-sorting system of claim 1, wherein the downstream portion of the flow channel splits into two or more outlet channels for separating a first portion of the sample flow enriched in microbubble-labeled cells from a second portion of the sample flow depleted of microbubble-labeled cells.

3. The cell-sorting system of claim 2, wherein the flow cell comprises a recirculating channel fluidically connecting an inlet coupled with the upstream portion and an outlet of the one or more outlets coupled with the downstream portion of the flow channel, the recirculating channel being configured to return the second portion of the flow depleted of microbubble-labeled cells back into the flow cell.

4. The cell-sorting system of claim 2, wherein at least one outlet of the one or more outlets is configured to receive the first portion of the sample comprising the displaced microbubble-labeled cells.

5. The cell-sorting system of claim 4, wherein the at least one outlet of the one or more outlets is fluidically coupled with a cell collector, to collect the first portion of the sample comprising the displaced microbubble-labeled cells into the cell collector.

6. The cell-sorting system of claim 1, further comprising two or more transducers.

7. The cell-sorting system of claim 6, where the two or more transducers are configured to produce different respective frequencies, to separate two or more populations of microbubble-labeled cells from each other and from the unlabeled cells.

8. The cell-sorting system of claim 1, wherein the acoustic radiation force displaces microbubble-labeled cells by at least 0.1 mm.

9. The cell-sorting system of claim 1, further comprising a disrupting chamber fluidically coupled with an outlet channel of the one or more outlet channels and configured to create overpressure on the outlet channel, wherein the overpressure is sufficient to rupture microbubbles of the microbubble labeled cells.

10. The cell-sorting system of claim 1, further comprising:

one or more attenuators acoustically coupled with the flow cell and positioned relative to the one or more acoustic transducers to absorb the traveling acoustic wave and to reduce reflection of the travelling acoustic wave in the flow channel.

* * * * *